United States Patent [19]
Fukumi et al.

[11] Patent Number: 5,294,623
[45] Date of Patent: Mar. 15, 1994

[54] (BENZHYDRYLOXYETHYLPIPERIDYL) ALIPHATIC ACID DERIVATIVES AND THEIR USE IN THE TREATMENT OF ALLERGIES AND ASTHMA

[75] Inventors: Hiroshi Fukumi; Toshiaki Sakamoto; Mitsuo Sugiyama; Yoshio Iizuka; Takeshi Yamaguchi, all of Tokyo, Japan

[73] Assignee: Sankyo Company, Limited, Tokyo, Japan

[21] Appl. No.: 995,547

[22] Filed: Dec. 22, 1992

Related U.S. Application Data

[63] Continuation of Ser. No. 668,133, Mar. 12, 1991, abandoned.

[30] Foreign Application Priority Data

Aug. 9, 1990 [JP] Japan ................. 2-212752

[51] Int. Cl.$^5$ .................. A01N 41/02; C07D 211/18
[52] U.S. Cl. .................. 514/317; 546/232; 546/235; 546/239
[58] Field of Search .................. 541/732, 735, 739; 514/317

[56] References Cited

U.S. PATENT DOCUMENTS 2,567,351  9/1961  Rieveschl ................ 546/236
4,957,927  9/1990  Ferrand et al. ................ 546/236

FOREIGN PATENT DOCUMENTS 0259227  3/1988  European Pat. Off.
63-68564  3/1988  Japan
2-212472  8/1990  Japan Primary Examiner—C. Warren Ivy
Assistant Examiner—Raymond Covington
Attorney, Agent, or Firm—Frishauf, Holtz, Goodman & Woodward

[57] ABSTRACT

Compounds of formula (I):

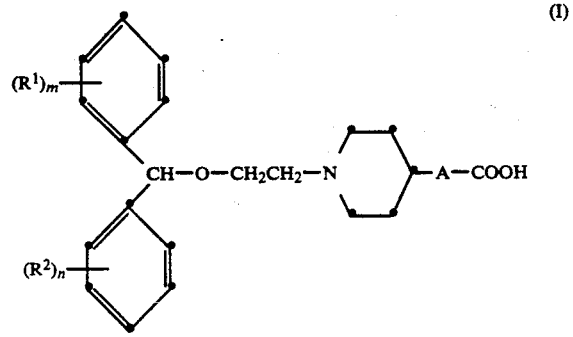

in which: $R^1$ and $R^2$ are independently alkyl, alkoxy, trifluoromethyl, nitro or halogen; A is an aliphatic hydrocarbon group having from 2 to 8 carbon atoms whose chain contains at least 2 carbon atoms in a linear chain between the piperidine group and —COOH, said group optionally being unsaturated; and m and n are independently 0, 1, 2 or 3; and pharmaceutically acceptable salts and esters thereof have been found to have valuable anti-histamine properties without the usual side effects of anti-histamines. Methods of preparing the compounds are also provided.

55 Claims, No Drawings

(BENZHYDRYLOXYETHYLPIPERIDYL) ALIPHATIC ACID DERIVATIVES AND THEIR USE IN THE TREATMENT OF ALLERGIES AND ASTHMA

This application is a continuation of application Ser. No. 07/668,133, filed Mar. 12, 1991, now abandoned.

BACKGROUND TO THE INVENTION

The present invention relates to a series of new 1-[(2-benzhydryloxyethyl)-4-piperidyl]aliphatic acid derivatives which have excellent anti-histamine, anti-allergic and anti-asthma activities without exhibiting the side effects so common with compounds having this type of activity. The invention also provides methods and compositions using these compounds as well as processes for their preparation.

Certain 1-[(2-benzhydryloxyethyl)-4-piperidyl]acetic acid derivatives having an activity similar to that of the compounds of the present invention are disclosed in Japanese Patent Application Kokai No. Sho. 63-68564 (equivalent to European Patent Publication No. 259 227), but the activities of the compounds of the present invention are substantially better than those of the compounds of this prior art; the compounds of the present invention also have a potent inhibitory effect on the accumulation of eosinophile in the bronchoalveolar lavage fluid and do not have the side effects common to most anti-histamines, notably sedative effects (commonly drowsiness), dryness of the oral mucosa etc. They also have a low toxicity and are therefore expected to find widespread applications in the treatment and prophylaxis of histamine-related disorders. Particularly asthma and allergies.

In addition to the prior art referred to above, Japanese Patent Application Kokai No. Hei. 2-212472, which was published after the priority dates hereof, but before the filing date, discloses certain 1-[(2-benzhydryloxyethyl)-4-piperidyl]acetic acid derivatives which have an activity similar to that of the compounds of the present invention, but which are different in that the compounds of the present invention possess other aliphatic acid groups than the acetic acid group of the prior art compounds.

BRIEF SUMMARY OF INVENTION

It is an object of the present invention to provide a series of novel 1-[(2-benzhydryloxyethyl)-4-piperidyl]aliphatic acid derivatives which have anti-histamine and related activities.

It is a further object of the invention to provide such compounds which have excellent anti-histamine, and hence anti-allergic and anti-asthma, activities without exhibiting significant side effects.

Other objects and advantages of the invention will become apparent as the description proceeds.

In accordance with the present invention, there are provided new compounds which may be represented by the formula (I):

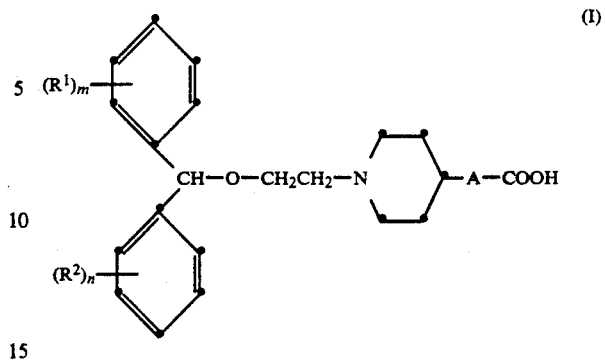

in which:
each of the groups or atoms represented by $R^1$ and $R^2$ is independently selected from the group consisting of alkyl groups having from 1 to 6 carbon atoms, alkoxy groups having from 1 to 6 carbon atoms, trifluoromethyl groups, nitro groups and halogen atoms;
A represents a straight or branched chain aliphatic hydrocarbon group having from 2 to 8 carbon atoms whose chain contains at least 2 carbon atoms in a linear chain between the piperidine group and —COOH, said group being saturated or including at least one double or triple carbon-carbon bond; and
m and n are independently 0, 1, 2 or 3;
and pharmaceutically acceptable salts and esters thereof The invention also provides a composition for the treatment or prophylaxis of histamine-related disorders, such as allergies or asthma, in a mammal, e.g. a human being, which comprises an effective amount of an anti-histamine in admixture with a pharmaceutically acceptable carrier or diluent, wherein the anti-histamine is at least one compound selected from the group consisting of compounds of formula (I) and pharmaceutically acceptable salts and esters thereof.

The invention also provides a method for the treatment or prophylaxis of histamine-related disorders, such as allergies or asthma, in a mammal, e.g. a human being, which comprises administering to said mammal an effective amount of an anti-histamine, wherein the anti-histamine is at least one compound selected from the group consisting of compounds of formula (I) and pharmaceutically acceptable salts and esters thereof.

The invention also provides novel processes for the preparation of the compounds of the present invention, which processes are described in more detail hereafter.

DETAILED DESCRIPTION OF INVENTION

In the compounds of the present invention, where $R^1$ or $R^2$ represents an alkyl group, this may be a straight or branched chain alkyl group having from 1 to 6 carbon atoms. Examples of such groups include the methyl, ethyl, propyl, isopropyl, butyl, isobutyl, sec-butyl, t-butyl, pentyl, isopentyl, t-pentyl, neopentyl, hexyl, isohexyl, 2-methylbutyl, 4-methylpentyl, 3-methylpentyl, 2-methylpentyl, 3,3-dimethylbutyl, 2,2-dimethylbutyl, 1,1-dimethylbutyl, 1,2-dimethylbutyl, 1,3-dimethylbutyl and 2,3-dimethylbutyl groups, of which we prefer those alkyl groups containing from 1 to 4 carbon atoms, particularly the methyl, ethyl, propyl, isopropyl, butyl and isobutyl groups. Of these, the methyl group is the more preferred.

Where $R^1$ or $R^2$ represents an alkoxy group, this may be a straight or branched chain alkoxy group having from 1 to 6 carbon atoms. Examples of such groups include the methoxy, ethoxy, propoxy, isopropoxy, butoxy, isobutoxy, sec-butoxy, t-butoxy, pentyloxy, isopentyloxy, t-pentyloxy, neopentyloxy, hexyloxy, isohexyloxy, 2-methylbutoxy, 4-methylpentyloxy, 3-methylpentyloxy, 2-methylpentyloxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups, of which we prefer those alkoxy groups containing from 1 to 4 carbon atoms, particularly the methoxy, ethoxy, propoxy, isopropoxy, butoxy and isobutoxy groups. Of these, the methoxy group is the more preferred.

Where $R^1$ or $R^2$ represents a halogen atom, it may be a fluorine, chlorine, bromine or iodine atom and is preferably a fluorine or chlorine atom.

Where there are two or three groups or atoms represented by $R^1$, these may be the same or different; and, similarly, where there are two or three groups or atoms represented by $R^2$, these may be the same or different. In general, however, we prefer those compounds in which m and n, which may be the same or different, are each 0 or 1. Where there is just one substituent $R^1$ and/or $R^2$ on a phenyl group of the benzhydryl moiety this can be at any of the o-, m- or p-positions, but it is preferably at the o- or p-position and more preferably at the p-position. We prefer those compounds in which one of m and n is 1 and the other is 0 or 1, and more preferably both m and n are 1. Preferably $R^1$ and $R^2$ are alkyl groups containing from 1 to 4 carbon atoms, alkoxy groups containing from 1 to 4 carbon atoms or halogen atoms, more preferably halogen atoms, and most preferably fluorine atoms.

A represents a straight or branched chain aliphatic hydrocarbon group having from 2 to 8 carbon atoms. This chain contains at least 2 carbon atoms in a linear chain between the piperidine group and the carboxy group, —COOH, although, provided that the limit of 8 carbon atoms in total is observed, that chain may have alkyl side chains. The group represented by A may be saturated or it may include at least one double or triple carbon-carbon bond. Where the group is unsaturated, it preferably has 1 or 2 unsaturated carbon-carbon double or triple bonds, and more preferably it has 1 or 2 double bonds, 1 triple bond or 1 double bond and 1 triple bond.

Examples of saturated groups which may be represented by A include the ethylene, trimethylene, propylene (1- or 2- methylethylene), tetramethylene, 1-methyltrimethylene, 2-methyltrimethylene, 3-methyltrimethylene, pentamethylene, 1-methyltetramethylene, 1-propylethylene, hexamethylene, 1-methylpentamethylene, 1-propyltrimethylene, heptamethylene, 1-propyltetramethylene, octamethylene and 1-propylpentamethylene groups. Examples of unsaturated groups include the vinylene (—CH=CH—), 1-methylvinylene [—CH=C(CH₃)—], 1-propenylene (—CH₂—CH=CH—), 2-propenylene (—CH=CH—CH₂—), 1-butenylene (—CH₂CH₂—CH=CH—), 3-butenylene (—CH=CH—CH₂CH₂—), 1,3-butadienylene (—CH=CH—CH=CH—), 1-methyl-1-butenylene [—CH₂CH₂—CH=C(CH₃)—], 1-pentenylene [—(CH₂)₃—CH=CH—], 4-pentenylene [—CH=CH—(CH₂)₃—], 1-propargylvinylene [—CH=C(CH₂C=CH)—], 1-methyl-1-pentenylene [—(CH₂)₃—CH=C(CH₃)—], 1-hexenylene [—(CH₂)₄—CH=CH—], 5-hexenylene [—CH=CH—(CH₂)₄—], 1-heptenylene [—(CH₂)₅—CH=CH—], 1,3-heptadienylene [—(CH₂)₃—CH=CH—CH=CH—] and 1-octenylene [—(CH₂)₆—CH=

CH—] groups. Of these, we prefer those alkylene groups having from 2 to 7 carbon atoms and those alkenylene groups having 2 or 3 carbon atoms, such as the vinylene, trimethylene, pentamethylene, heptamethylene, 1-methylethylene, 1-methyltrimethylene, 1-methyltetramethylene and 1-propenylene groups, and we more prefer the alkylene groups having 3 or 5 carbon atoms.

For the avoidance of doubt, in the preceding paragraph, the groups are numbered with the carbon atom adjacent the carboxy, —COOH, group in formula (I) as the 1-position.

The compounds of formula (I) are carboxylic acids and can, therefore, form esters with suitable alcohols. There is no particular restriction on the nature of the ester, provided that, where it is to be used in therapy, it is pharmaceutically acceptable, i.e. its activity is not reduced (or unacceptably reduced) and its toxicity is not increased (or unacceptably increased) as compared with the free acid. Since it is believed that the active agent is probably the carboxylic acid, the nature of the ester group will not have a fundamental effect on activity, and any apparent difference in activity between two different esters of the same carboxylic acid is thought to be a function of different rates of absorption by the mammalian metabolism. Hence, for therapeutic use, the ester group should be chosen to optimise absorption, as is well known in the art.

The esters of the present invention may be represented by the formula (Ia):

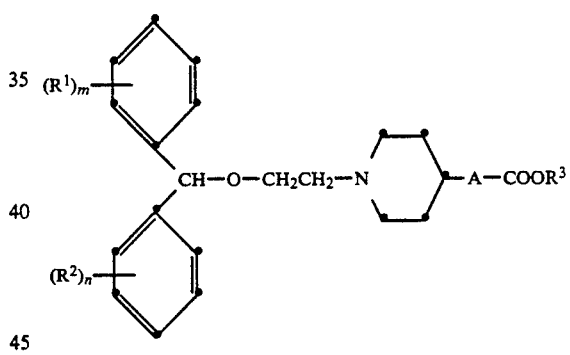

(Ia)

in which: $R^1$, $R^2$, A, m and n are as defined above and R is an ester group.

Examples of ester groups which may be represented by $R^3$ in the compounds of the present invention include:

$C_1$-$C_{20}$ alkyl groups, more preferably $C_1$-$C_6$ alkyl groups, such as those exemplified in relation to $R^1$ and $R^2$, and higher alkyl groups as are well known in the art, such as the heptyl, 1-methylhexyl, 2-methylhexyl, 5-methylhexyl, 3-ethylpentyl, octyl, 2-methylheptyl, 5-methylheptyl, 2-ethylhexyl, 2-ethyl-3-methylpentyl, 3-ethyl-2-methylpentyl, nonyl, 2-methyloctyl, 7-methyloctyl, 4-ethylheptyl, 3-ethyl-2-methylhexyl, 2-ethyl-1-methylhexyl, decyl, 2-methylnonyl, 8-methylnonyl, 5-ethyloctyl, 3-ethyl-2-methylheptyl, 3,3-diethylhexyl, undecyl, 2-methyldecyl, 9-methyldecyl, 4-ethylnonyl, 3,5-dimethylnonyl, 3-propyloctyl, 5-ethyl-4-methyloctyl, dodecyl, 1-methylundecyl, 10-methylundecyl, 3-ethyldecyl, 5-propylnonyl, 3,5-diethyloctyl, tridecyl, 11-methyldodecyl, 7-ethylundecyl, 4-propyldecyl, 5-ethyl-3-methyldecyl, 3-pentyloctyl, tetradecyl, 12-methyltridecyl, 8-ethyldodecyl, 6- propylundecyl, 4-butyldecyl, 2-pentylnonyl, pentadecyl, 13-methyltetradecyl, 10-ethyltridecyl, 7-propyldodecyl, 5-ethyl-3-methyldodecyl, 4-pentyldecyl, hexadecyl, 14-methylpentadecyl, 6-ethyltetradecyl, 4-propyltridecyl, 2-butyldodecyl, heptadecyl, 15-methylhexadecyl, 7-ethylpentadecyl, 3-propyltetradecyl, 5-pentyldodecyl, octadecyl, 16-methylheptadecyl, 5-propylpentadecyl, nonadecyl, 17-methyloctadecyl, 4-ethylheptadecyl, icosyl, 18-methylnonadecyl and 3-ethyloctadecyl groups, but still more preferably the $C_1$–$C_4$ alkyl groups and most preferably the methyl and ethyl groups:

$C_3$–$C_7$ cycloalkyl groups, for example the cyclopropyl, cyclobutyl, cyclopentyl, cyclohexyl or cycloheptyl group;

aralkyl groups in which the aromatic group is $C_6$–$C_{14}$, which may be substituted, preferably on its aryl moiety, or unsubstituted, and, if substituted, may have at least one substituent selected from the group consisting of the groups and atoms which may be represented by $R^1$ and $R^2$; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 2-nitrobenzyl, 4-methoxybenzyl and piperonyl groups, and preferred groups include the benzyl and phenethyl groups;

alkenyl groups having from 2 to 6 car preferred groups include the allyl and 2-methylallyl groups;

aryl groups having from 6 to 10 carbon atoms, especially phenyl or naphthyl groups, and preferably phenyl groups, in which the phenyl group is unsubstituted or substituted, preferably with at least one $C_1$–$C_4$ alkyl or $C_1$–$C_4$ alkoxy group or halogen atom, for example the phenyl, tolyl and methoxyphenyl groups;

phenacyl groups, which may be unsubstituted or have at least one substituent selected from the groups and atoms which may be represented by $R^1$ and $R^2$, for example the phenacyl group itself or the p-bromophenacyl group;

cyclic and acyclic terpenyl groups, for example the geranyl, neryl, linalyl, phytyl, menthyl (especially m- and p- menthyl), thujyl, caryl, pinanyl, bornyl, norcaryl, norpinanyl, norbornyl, menthenyl, camphenyl and norbornenyl groups;

terpenylcarbonyloxyalkyl and terpenyloxycarbonyloxyalkyl groups, in which the terpenyl group is as exemplified above, and is preferably a cyclic terpenyl group for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

alkoxymethyl groups, in which the alkoxy part is $C_1$–$C_6$, preferably $C_1$–$C_4$, and may itself be substituted by a single unsubstituted alkoxy group, such as the methoxymethyl, ethoxymethyl, propoxymethyl, isopropoxymethyl, butoxymethyl and methoxyethoxymethyl groups;

alkoxycarbonylmethyl groups in which the alkoxy part has from 1 to 6 carbon atoms, preferably from 1 to 4 carbon atoms, such as the methoxycarbonylmethyl, ethoxycarbonylmethyl, propoxycarbonylmethyl, isopropoxycarbonylmethyl and butoxycarbonylmethyl groups; and preferred groups include the methoxycarbonylmethyl and ethoxycarbonylmethyl groups;

aliphatic acyloxymethyl groups, in which the acyl group is preferably an alkanoyl group and is more preferably a $C_2$–$C_6$ alkanoyl group, such as the acetoxymethyl, propionyloxymethyl, butyryloxymethyl, isobutyryloxymethyl and pivaloyloxymethyl groups; and preferred groups include the pivaloyloxymethyl group;

higher aliphatic acyloxyalkyl groups in which the acyl group is preferably an alkanoyl group and is more preferably a $C_2$–$C_6$ alkanoyl group, and the alkyl part is $C_2$–$C_6$, and preferably $C_2$–$C_4$, such as the 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

alkoxycarbonyloxyalkyl groups, especially 1-(alkoxycarbonyloxy)ethyl groups, in which the alkoxy part is $C_1$–$C_{10}$, preferably $C_1$–$C_6$, and more preferably $C_1$–$C_4$, and the alkyl part is $C_1$–$C_6$, preferably $C_1$–$C_4$, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups are $C_1$–$C_6$, preferably $C_1$–$C_4$, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups; and preferred groups include the 1-methoxycarbonyloxyethyl and 1-ethoxycarbonyloxyethyl groups;

(5-alkyl- or 5-phenyl- 2-oxo-1,3-dioxolen-4-yl)alkyl groups in which the alkyl or each alkyl group (which may be the same or different) is $C_1$–$C_6$, preferably $C_1$–$C_4$, and the phenyl group may be unsubstituted or substituted by at least one of the groups and atoms represented by $R^1$ and $R^2$, for example the (5-alkyl- or 5-phenyl- 2-oxo-1,3-dioxolen-4-yl)methyl groups, especially the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and preferred groups include the (5-methyl-2-oxo-1,3-dioxolen-4-yl)methyl and (5-phenyl-2-oxo-1,3-dioxolen-4-yl)methyl groups; and other groups, especially groups which are easily removed in vivo, such as the phthalidyl, indanyl and 2-oxo-4,5,6,7-tetrahydro-1,3-benzodioxolen-4-yl groups.

Of the above groups, we especially prefer the alkyl groups having from 1 to 4 carbon atoms and those groups which can be removed easily in vivo, and more preferably the pivaloyloxymethyl, methoxycarbonylmethyl, ethoxycarbonylmethyl, 1-methoxycarbonyloxyethyl, 1-ethoxycarbonyloxyethyl, (5-methyl-2-oxo-1,3-dioxolen-4-yl)methyl, (5-phenyl-2-oxo-1,3-dioxolen-4-yl)methyl and phthalidyl groups, and most preferably the alkyl groups having from 1 to 4 carbon atoms.

The compounds of the present invention can also form salts with a cation, for example:

metal atoms, especially: alkali metal atoms, such as the sodium, potassium and lithium atoms; alkaline earth metal atoms, such as the calcium and barium atoms; and other atoms, such as the iron, magnesium and aluminum atoms:

the ammonium group;

cations derived from a trialkylamine, such as triethylamine or trimethylamine, or from another organic base, such as procaine, dibenzylamine, phenethylamine, 2-phenylethylbenzylamine, ethanolamine, diethanolamine, a polyhydroxyalkylamine or N-methylglucosamine; and basic amino acids, such as lysine, arginine, ornithine or histidine.

Of the above, we prefer salts of an alkaline metal or of a basic amino acid.

In addition, where the compounds are in the form of an ester of formula (Ia), they may form salts with an acid, for example:

with a mineral acid, especially a hydrohalic acid, such as hydrochloric acid, hydrofluoric acid, hydrobromic acid or hydroiodic acid, or another mineral acid, such as sulfuric acid, nitric acid, perchloric acid, carbonic acid or phosphoric acid;

with an organic carboxylic acid, such as oxalic acid, maleic acid, succinic acid, umaric acid, tartaric acid or citric acid;

with a sulfonic acid, e.g. an alkanesulfonic or haloalkanesulfonic acid, such as methanesulfonic acid trifluoromethanesulfonic acid or ethanesulfonic acid, or with an arylsulfonic acid, such as benzenesulfonic acid or p-toluenesulfonic acid; and with an acidic amino acid, such as qlutamic acid or aspartic acid.

Of the above, we prefer salts of a mineral acid or of an organic carboxylic acid.

Those compounds of the present invention which contain a double bond may form cis and trans isomers. Additionally, the compounds may contain one or more asymmetric carbon atoms in their molecules and may thus form optical isomers. Although these are all represented herein by a single molecular formula, the present invention includes both the individual, isolated isomers and mixtures, including racemates thereof. Where stereospecific synthesis techniques are employed, individual isomers may be prepared directly; on the other hand, if a mixture of isomers is prepared, the individual isomers may be obtained by conventional resolution techniques.

A preferred class of compounds of the present invention are those compounds of formula (I'):

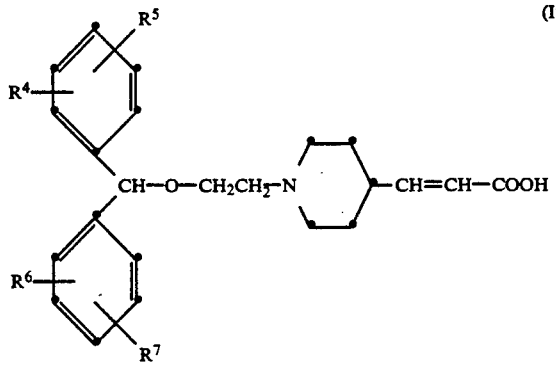

in which $R^4$, $R^5$, $R^6$ and $R^7$ are the same or different and each represents a hydrogen atom, an alkyl group having from 1 to 6 carbon atoms, an alkoxy group having from 1 to 6 carbon atoms, a trifluoromethyl group, a halogen atom or a nitro group;

and pharmaceutically acceptable salts and esters thereof.

Examples of the groups and atoms which may be represented by $R^4$, $R^5$, $R^6$ and $R^7$ are as given by way of example for $R^1$ and $R^2$.

A further preferred class of compounds of the present invention are those compounds of formula (I''):

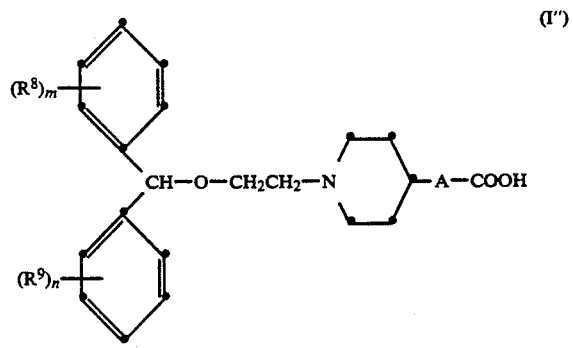

in which: A, m and n are as defined above, except that A is not a vinylene group; and $R^8$ and $R^9$ are the same or different and each represents an alkyl group having from 1 to 4 carbon atoms, an alkoxy group having from 1 to 4 carbon atoms or a halogen atom;

and pharmaceutically acceptable salts and esters thereof.

Examples of the groups and atoms which may be represented by $R^8$ and $R^9$ are as given by way of example for $R^1$ and $R^2$.

The other preferred classes of compounds of the present invention are those compounds of formula (I) and salts and esters thereof in which:

(a) $R^1$ and $R^2$ are the same or different and each represents a halogen atom;

(b) A represents an alkylene group having from 2 to 7 carbon atoms or an alkenylene group having 2 or 3 carbon atoms;

c) m and n are the same or different and each is 0 or 1; and (d) in the case of the esters, alkyl esters having from 1 to 4 carbon atoms in the alkyl moiety or esters which can easily be removed in vivo.

Of the above, especially preferred are those in which $R^1$ and $R^2$ are as defined in (a), A is as defined in (b) and m and n are as defined in (c), salts thereof and esters thereof as defined in (d).

Still more preferred compounds of the present invention are those compounds of formula (I) and salts and esters thereof in which:

(e) $R^1$ and $R^2$ are the same or different and each represents a fluorine or chlorine atom;

(f) A represents an alkylene group having 3 or 5 carbon atoms; and (g) in the case of the esters, alkyl esters having from 1 to 4 carbon atoms in the alkyl moiety.

Of the above, especially preferred are those in which $R^1$ and $R^2$ are as defined in (e), A is as defined in (f) and m and n are as defined in .(c), salts thereof and esters thereof as defined in (g).

Specific examples of compounds of the present invention are shown by the following formulae (I-1) and (I-2), in which the substituent groups are as defined by the corresponding one of Tables 1 and 2, i.e. formula (I-1) relates to Table 1 and formula (1-2) relates to Table 2. In the tables, the following abbreviations are used:

| | |
|---|---|
| Bu | butyl |
| iBu | isobutyl |
| Bz | benzyl |
| Dox | (5-methyl-2-oxo-1,3-dioxolen-4-yl)methyl |
| Et | ethyl |
| Etc | ethoxycarbonyl |
| Me | methyl |
| Pdox | (5-phenyl-2-oxo-1,3-dioxolen-4-yl)methyl |
| Ph | phenyl |
| Piv | pivaloyl |
| Pr | propyl |
| iPr | isopropyl |

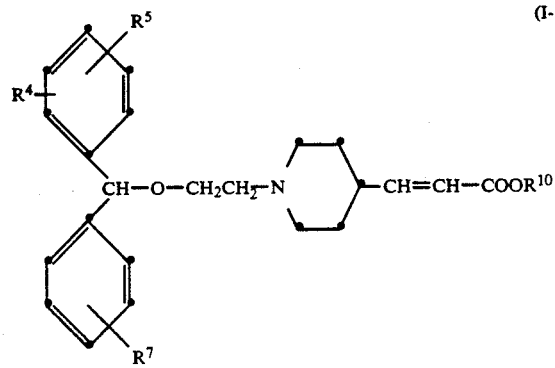

(I-1)

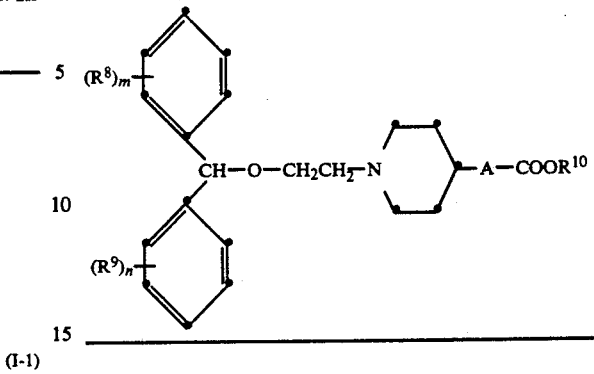

(I-2)

TABLE 1

| Compound No. | $R^4$ | $R^5$ | $R^7$ | $R^{10}$ |
|---|---|---|---|---|
| 1-1 | 4-F | H | 4-F | H |
| 1-2 | 4-Cl | H | 4-Cl | H |
| 1-3 | H | H | H | Me |
| 1-4 | H | H | H | Et |
| 1-5 | 4-F | H | H | Me |
| 1-6 | 4-F | H | H | Et |
| 1-7 | 4-Cl | H | H | Me |
| 1-8 | 4-Cl | H | H | Et |
| 1-9 | 4-Cl | H | H | Ph |
| 1-10 | 4-Me | H | H | Et |
| 1-11 | 4-MeO | H | H | Et |
| 1-12 | 4-CF$_3$ | H | H | iPr |
| 1-13 | 4-CF$_3$ | H | H | iBu |
| 1-14 | 4-NO$_2$ | H | H | Bz |
| 1-15 | 4-F | H | 4-F | Me |
| 1-16 | 4-F | H | 4-F | Et |
| 1-17 | 4-Cl | H | 4-Cl | Me |
| 1-18 | 4-Cl | H | 4-Cl | Et |
| 1-19 | 2-F | H | 4-F | Me |
| 1-20 | 2-F | H | 4-F | Et |
| 1-21 | 2-Cl | H | 4-F | Me |
| 1-22 | 2-Cl | H | 4-F | Et |
| 1-23 | 2-Cl | H | 4-Cl | Et |
| 1-24 | 3-Cl | H | 4-Cl | Me |
| 1-25 | 2-Cl | 4-Cl | H | Me |
| 1-26 | 3-Cl | 4-Cl | H | Et |
| 1-27 | 3-Cl | 4-Cl | H | iPr |

TABLE 2

| Compound No. | $(R^8)_m$ | $(R^9)_n$ | A | $R^{10}$ |
|---|---|---|---|---|
| 2-1 | H | H | —(CH$_2$)$_3$— | H |
| 2-2 | H | H | —(CH$_2$)$_3$— | Me |
| 2-3 | H | H | —(CH$_2$)$_3$— | Et |
| 2-4 | H | H | —(CH$_2$)$_5$— | H |
| 2-5 | H | H | —(CH$_2$)$_5$— | Me |
| 2-6 | H | H | —(CH$_2$)$_5$— | Et |
| 2-7 | H | H | —(CH$_2$)$_7$— | H |
| 2-8 | H | H | —(CH$_2$)$_7$— | Et |
| 2-9 | H | H | —CH$_2$CH(Me)— | Et |
| 2-10 | H | H | —(CH$_2$)$_2$CH(Me)— | Et |
| 2-11 | H | H | —(CH$_2$)$_4$CH(Me)— | Et |
| 2-12 | H | H | —(CH$_2$)$_3$CH=CH— | Et |
| 2-13 | H | 4-Cl | —(CH$_2$)$_3$— | H |
| 2-14 | H | 4-Cl | —(CH$_2$)$_3$— | Me |
| 2-15 | H | 4-Cl | —(CH$_2$)$_3$— | Et |
| 2-16 | H | 4-Cl | —(CH$_2$)$_5$— | H |

TABLE 2-continued

| Compound No. | $(R^8)_m$ | $(R^9)_n$ | A | $R^{10}$ |
|---|---|---|---|---|
| 2-17 | H | 4-Cl | $-(CH_2)_5-$ | Et |
| 2-18 | H | 4-Cl | $-(CH_2)_5-$ | Me |
| 2-19 | H | 4-Cl | $-(CH_2)_7-$ | Et |
| 2-20 | H | 4-Cl | $-CH_2CH(Me)-$ | Et |
| 2-21 | H | 4-Cl | $-(CH_2)_2CH(Me)-$ | Et |
| 2-22 | H | 4-Cl | $-(CH_2)_4CH(Me)-$ | iPr |
| 2-23 | H | 4-Cl | $-(CH_2)_4CH(Me)-$ | Et |
| 2-24 | H | 4-Cl | $-(CH_2)_3CH=CH-$ | Et |
| 2-25 | 4-Cl | 4-Cl | $-(CH_2)_2-$ | H |
| 2-26 | 4-Cl | 4-Cl | $-(CH_2)_2-$ | Me |
| 2-27 | 4-Cl | 4-Cl | $-(CH_2)_2-$ | Et |
| 2-28 | 4-Cl | 4-Cl | $-(CH_2)_2-$ | Pr |
| 2-29 | 4-Cl | 4-Cl | $-(CH_2)_2-$ | Bu |
| 2-30 | 4-Cl | 4-Cl | $-(CH_2)_3-$ | H |
| 2-31 | 4-Cl | 4-Cl | $-(CH_2)_3-$ | Me |
| 2-32 | 4-Cl | 4-Cl | $-(CH_2)_3-$ | Et |
| 2-33 | 4-Cl | 4-Cl | $-(CH_2)_3-$ | Pr |
| 2-34 | 4-Cl | 4-Cl | $-(CH_2)_3-$ | iBu |
| 2-35 | 4-Cl | 4-Cl | $-(CH_2)_5-$ | H |
| 2-36 | 4-Cl | 4-Cl | $-(CH_2)_5-$ | Me |
| 2-37 | 4-Cl | 4-Cl | $-(CH_2)_5-$ | Et |
| 2-38 | 4-Cl | 4-Cl | $-(CH_2)_7-$ | H |
| 2-39 | 4-Cl | 4-Cl | $-(CH_2)_7-$ | Me |
| 2-40 | 4-Cl | 4-Cl | $-(CH_2)_7-$ | Et |
| 2-41 | 4-Cl | 4-Cl | $-(CH_2)_7-$ | Pr |
| 2-42 | 4-Cl | 4-Cl | $-CH_2CH(Me)-$ | Me |
| 2-43 | 4-Cl | 4-Cl | $-CH_2CH(Me)-$ | Et |
| 2-44 | 4-Cl | 4-Cl | $-(CH_2)_2CH(Me)-$ | Me |
| 2-45 | 4-Cl | 4-Cl | $-(CH_2)_2CH(Me)-$ | Et |
| 2-46 | 4-Cl | 4-Cl | $-(CH_2)_4CH(Me)-$ | Et |
| 2-47 | 4-Cl | 4-Cl | $-(CH_2)_3CH=CH-$ | Et |
| 2-48 | H | 4-F | $-(CH_2)_2-$ | H |
| 2-49 | H | 4-F | $-(CH_2)_2-$ | Me |
| 2-50 | H | 4-F | $-(CH_2)_2-$ | Et |
| 2-51 | H | 4-F | $-(CH_2)_2-$ | iPr |
| 2-52 | H | 4-F | $-(CH_2)_3-$ | H |
| 2-53 | H | 4-F | $-(CH_2)_3-$ | Me |
| 2-54 | H | 4-F | $-(CH_2)_3-$ | Pr |
| 2-55 | H | 4-F | $-(CH_2)_5-$ | H |
| 2-56 | H | 4-F | $-(CH_2)_5-$ | Me |
| 2-57 | H | 4-F | $-(CH_2)_5-$ | Et |
| 2-58 | H | 4-F | $-(CH_2)_7-$ | H |
| 2-59 | H | 4-F | $-(CH_2)_7-$ | Me |
| 2-60 | H | 4-F | $-(CH_2)_7-$ | Et |
| 2-61 | H | 4-F | $-(CH_2)_7-$ | Pr |
| 2-62 | H | 4-F | $-CH_2CH(Me)-$ | Et |

TABLE 2-continued

| Compound No. | $(R^8)_m$ | $(R^9)_n$ | A | $R^{10}$ |
|---|---|---|---|---|
| 2-63 | H | 4-F | $-(CH_2)_2CH-$<br>                \|<br>                Me | Et |
| 2-64 | H | 4-F | $-(CH_2)_4CH-$<br>                \|<br>                Me | Et |
| 2-65 | H | 4-F | $-(CH_2)_3CH=CH-$ | Et |
| 2-66 | H | 4-F | $-(CH_2)_2-$ | H |
| 2-67 | H | 4-F | $-(CH_2)_2-$ | Me |
| 2-68 | 4-F | 4-F | $-(CH_2)_2-$ | Et |
| 2-69 | 4-F | 4-F | $-(CH_2)_2-$ | Pr |
| 2-70 | 4-F | 4-F | $-(CH_2)_3-$ | H |
| 2-71 | 4-F | 4-F | $-(CH_2)_3-$ | Me |
| 2-72 | 4-F | 4-F | $-(CH_2)_3-$ | Et |
| 2-73 | 4-F | 4-F | $-(CH_2)_3-$ | iPr |
| 2-74 | 4-F | 4-F | $-(CH_2)_3-$ | iBu |
| 2-75 | 4-F | 4-F | $-(CH_2)_5-$ | H |
| 2-76 | 4-F | 4-F | $-(CH_2)_5-$ | Me |
| 2-77 | 4-F | 4-F | $-(CH_2)_5-$ | Et |
| 2-78 | 4-F | 4-F | $-(CH_2)_5-$ | Pr |
| 2-79 | 4-F | 4-F | $-(CH_2)_7-$ | H |
| 2-80 | 4-F | 4-F | $-(CH_2)_7-$ | Me |
| 2-81 | 4-F | 4-F | $-(CH_2)_7-$ | Et |
| 2-82 | 4-F | 4-F | $-(CH_2)_7-$ | Pr |
| 2-83 | 4-F | 4-F | $-CH_2CH-$<br>            \|<br>            Me | H |
| 2-84 | 4-F | 4-F | $-CH_2CH-$<br>            \|<br>            Me | Me |
| 2-85 | 4-F | 4-F | $-CH_2CH-$<br>            \|<br>            Me | Et |
| 2-86 | 4-F | 4-F | $-(CH_2)_2CH-$<br>                \|<br>                Me | H |
| 2-87 | 4-F | 4-F | $-(CH_2)_2CH-$<br>                \|<br>                Me | Me |
| 2-88 | 4-F | 4-F | $-(CH_2)_2CH-$<br>                \|<br>                Me | Et |
| 2-89 | 4-F | 4-F | $-(CH_2)_4CH-$<br>                \|<br>                Me | H |
| 2-90 | 4-F | 4-F | $-(CH_2)_4CH-$<br>                \|<br>                Me | Et |
| 2-91 | 4-F | 4-F | $-(CH_2)_3CH=CH-$ | Et |
| 2-92 | 4-F | 4-F | $-CH=C-$<br>          \|<br>          Me | Et |
| 2-93 | 4-F | 4-F | $-CH=C-$<br>          \|<br>          $CH_2C\equiv CH$ | Et |
| 2-94 | 4-F | 4-F | $-CH=CH-CH=CH-$ | Et |
| 2-95 | 4-F | 4-F | $-(CH_2)_2CH=CH-$ | Et |
| 2-96 | 4-F | 4-F | $-(CH_2)_2CH=C-$<br>                   \|<br>                   Me | Et |

TABLE 2-continued

| Compound No. | $(R^8)_m$ | $(R^9)_n$ | A | $R^{10}$ |
|---|---|---|---|---|
| 2-97 | 4-F | 4-F | $-(CH_2)_3CH=C(Me)-$ | Et |
| 2-98 | 4-F | 4-F | $-(CH_2)_3CH=CH-CH=CH-$ | Et |
| 2-99 | 4-F | 4-F | $-(CH_2)_4CH=CH-$ | Et |
| 2-100 | 4-F | 4-F | $-CH_2-CH=CH-CH=CH-$ | Et |
| 2-101 | 4-F | 4-F | $-CH_2-CH(Et)-$ | Et |
| 2-102 | 4-F | 4-F | $-CH_2-CH(C_3H_7)-$ | Et |
| 2-103 | 4-F | 4-F | $-(CH_2)_6-$ | Et |
| 2-104 | 4-F | 4-F | $-(CH_2)_3-CH(Me)-$ | Et |
| 2-105 | H | 4-Me | $-(CH_2)_2-$ | H |
| 2-106 | H | 4-Me | $-(CH_2)_2-$ | Et |
| 2-107 | H | 4-Me | $-(CH_2)_3-$ | H |
| 2-108 | H | 4-Me | $-(CH_2)_3-$ | Me |
| 2-109 | H | 4-Me | $-(CH_2)_3-$ | Et |
| 2-110 | H | 4-Me | $-(CH_2)_5-$ | H |
| 2-111 | H | 4-Me | $-(CH_2)_5-$ | Me |
| 2-112 | H | 4-Me | $-(CH_2)_5-$ | Et |
| 2-113 | H | 4-Me | $-(CH_2)_7-$ | H |
| 2-114 | H | 4-Me | $-(CH_2)_7-$ | Me |
| 2-115 | H | 4-Me | $-(CH_2)_7-$ | Et |
| 2-116 | H | 4-Me | $-CH_2-CH(Me)-$ | H |
| 2-117 | H | 4-Me | $-CH_2-CH(Me)-$ | Me |
| 2-118 | H | 4-Me | $-CH_2-CH(Me)-$ | Et |
| 2-119 | H | 4-Me | $-(CH_2)_2-CH(Me)-$ | Et |
| 2-120 | H | 4-Me | $-(CH_2)_4-CH(Me)-$ | Et |
| 2-121 | H | 4-Me | $-(CH_2)_3CH=CH-$ | Et |
| 2-122 | H | 4-Me | $-CH=C(Me)-$ | Et |
| 2-123 | 4-Me | 4-Me | $-(CH_2)_2-$ | H |
| 2-124 | 4-Me | 4-Me | $-(CH_2)_2-$ | Et |
| 2-125 | 4-Me | 4-Me | $-(CH_2)_3-$ | Me |
| 2-126 | 4-Me | 4-Me | $-(CH_2)_3-$ | Et |
| 2-127 | 4-Me | 4-Me | $-(CH_2)_3-$ | iPr |
| 2-128 | 4-Me | 4-Me | $-(CH_2)_5-$ | Me |
| 2-129 | 4-Me | 4-Me | $-(CH_2)_5-$ | Et |
| 2-130 | 4-Me | 4-Me | $-(CH_2)_7-$ | Me |
| 2-131 | 4-Me | 4-Me | $-(CH_2)_7-$ | Et |
| 2-132 | 4-Me | 4-Me | $-CH_2C(Me)-$ | Et |
| 2-133 | 4-Me | 4-Me | $-(CH_2)_2CH(Me)-$ | Et |

TABLE 2-continued

| Compound No. | $(R^8)_m$ | $(R^9)_n$ | A | $R^{10}$ |
|---|---|---|---|---|
| 2-134 | 4-Me | 4-Me | —(CH$_2$)$_4$CH(Me)— | Et |
| 2-135 | 4-Me | 4-Me | —(CH$_2$)$_3$CH=CH— | Et |
| 2-136 | 4-Me | 4-Me | —CH=C(Me)— | Et |
| 2-137 | H | 4-OMe | —(CH$_2$)$_2$— | Et |
| 2-138 | H | 4-OMe | —(CH$_2$)$_3$— | Et |
| 2-139 | H | 4-OMe | —(CH$_2$)$_5$— | Et |
| 2-140 | H | 4-OMe | —(CH$_2$)$_2$CH(Me)— | Et |
| 2-141 | 4-OMe | 4-OMe | —(CH$_2$)$_3$— | Et |
| 2-142 | H | H | —CH$_2$—CH=CH— | Et |
| 2-143 | H | 4-Cl | —CH$_2$—CH=CH— | Et |
| 2-144 | H | 4-F | —CH$_2$—CH=CH— | Et |
| 2-145 | H | 4-Me | —CH$_2$—CH=CH— | Et |
| 2-146 | 4-F | 4-F | —CH$_2$—CH=CH— | Et |
| 2-147 | H | 2-Cl | —(CH$_2$)$_3$— | Et |
| 2-148 | H | 2-Cl | —(CH$_2$)$_5$— | Et |
| 2-149 | H | 2-F | —(CH$_2$)$_3$— | Et |
| 2-150 | H | 2-F | —(CH$_2$)$_5$— | Et |
| 2-151 | H | 3-F | —(CH$_2$)$_3$— | Et |
| 2-152 | H | 3-F | —(CH$_2$)$_5$— | Et |
| 2-153 | 4-F | 2-F | —(CH$_2$)$_3$— | Et |
| 2-154 | 4-F | 2-F | —(CH$_2$)$_5$— | Et |
| 2-155 | 4-F | 2-Cl | —(CH$_2$)$_3$— | Et |
| 2-156 | 4-F | 2-Cl | —(CH$_2$)$_5$— | Et |
| 2-157 | H | 2,4-diCl | —(CH$_2$)$_3$— | Et |
| 2-158 | H | 2,4-diCl | —(CH$_2$)$_5$— | Et |
| 2-159 | H | 3,5-diCl | —(CH$_2$)$_3$— | Et |
| 2-160 | H | 3,5-diCl | —(CH$_2$)$_5$— | Et |
| 2-161 | H | 3,4-diCl | —(CH$_2$)$_3$— | Et |
| 2-162 | H | 3,4-diCl | —(CH$_2$)$_5$— | Et |
| 2-163 | H | 2,5-diCl | —(CH$_2$)$_3$— | Et |
| 2-164 | H | 2,5-diCl | —(CH$_2$)$_5$— | Et |
| 2-165 | H | 3,4-diF | —(CH$_2$)$_3$— | Et |
| 2-166 | H | 3,4-diF | —(CH$_2$)$_5$— | Et |
| 2-167 | H | 2,5-diF | —(CH$_2$)$_3$— | Et |
| 2-168 | H | 2,5-diF | —(CH$_2$)$_5$— | Et |
| 2-169 | H | 2,6-diF | —(CH$_2$)$_3$— | Et |
| 2-170 | H | 2,6-diF | —(CH$_2$)$_5$— | Et |
| 2-171 | 4-Cl | 3,5-diCl | —(CH$_2$)$_3$— | Et |
| 2-172 | 4-Cl | 3,5-diCl | —(CH$_2$)$_5$— | Et |
| 2-173 | 4-F | 3,5-diCl | —(CH$_2$)$_3$— | Et |
| 2-174 | 4-F | 3,5-diCl | —(CH$_2$)$_5$— | Et |
| 2-175 | 4-OMe | 3,5-diCl | —(CH$_2$)$_3$— | Et |
| 2-176 | 4-OMe | 3,5-diCl | —(CH$_2$)$_5$— | Et |
| 2-177 | 4-Me | 3,5-diCl | —(CH$_2$)$_3$— | Et |
| 2-178 | 4-Me | 3,5-diCl | —(CH$_2$)$_5$— | Et |
| 2-179 | 4-F | 4-F | —(CH$_2$)$_3$— | Pr |
| 2-180 | 4-F | 4-F | —(CH$_2$)$_3$— | Bu |
| 2-181 | 4-F | 4-F | —(CH$_2$)$_3$— | EtcCH$_2$— |
| 2-182 | 4-F | 4-F | —(CH$_2$)$_3$— | PivOCH$_2$— |
| 2-183 | 4-F | 4-F | —(CH$_2$)$_3$— | 1-EtcOEt— |
| 2-184 | 4-F | 4-F | —(CH$_2$)$_3$— | Dox |
| 2-185 | 4-F | 4-F | —(CH$_2$)$_3$— | Pdox |

Of the compounds listed above, the following compounds are preferred, that is to say Compounds No. 1-3, 1-4, 1-7, 1-8, 1-15, 1-16, 1-19, 1-20, 2-1, 2-2, 2-3, 2-14, 2-15, 2-32, 2-49, 2-50, 2-51, 2-53, 2-54, 2-67, 2-68, 2-70, 2-71, 2-72, 2-73, 2-74, 2-76, 2-77, 2-81, 2-84, 2-85, 2-88, 2-90, 2-91, 2-92, 2-93, 2-94, 2-95, 2-96, 2-97, 2-98, 2-99, 2-102, 2-104, 2-108, 2-109, 2-142, 2-143, 2-144, 2-145, 2-146, 2-149, 2-150, 2-151, 2-152, 2-153, 2-154, 2-155, 2-156, 2-165, 2-166, 2-179, 2-180, 2-181, 2-182, 2-183, 2-184 and 2-185, and the following are more preferred, that is to say Compounds No.:

-1-15. Methyl 3-{1-[2-bis(4-fluorophenyl)methoxyethyl]-4-piperidyl}acrylate;
-1-16. Ethyl 3-{1-[2-bis(4-fluorophenyl)methoxyethyl]-4-piperidyl}acrylate;
-2-71. Methyl 4-[1-[2-bis(4-fluorophenyl)methoxyethyl]-4-piperidyl}butyrate;
-2-72. Ethyl 4-{1-[2-bis(4-fluorophenyl)methoxyethyl]-4-piperidyl}butyrate;
2-76. Methyl 6-{1-[2-bis(4-fluorophenyl)methoxyethyl]-4-piperidyl}hexanoate;
2-77. Ethyl 6-{1-[2-bis(4-fluorophenyl)methoxyethyl]-4-piperidyl}hexanoate;

2-81. Ethyl 8-[1-[2-bis(4-fluorophenyl)methoxyethyl]-4-piperidyl}octanoate;

2-84. Methyl 3-{1-[2-bis(4-fluorophenyl)methoxyethyl]-4-piperidyl}-2-methylpropionate;

2-85. Ethyl 3-[1-[2-bis(4-fluorophenyl)methoxyethyl]-4-piperidyl]-2-methylpropionate:

2-90. Ethyl 6-{1-[2-bis(4-fluorophenyl)methoxyethyl]-4-piperidyl}-2-methylhexanoate;

2-91. Ethyl 6-[1-[2-bis(4-fluorophenyl)methoxyethyl]-4-piperidyl}-2-hexenoate;

2-153. Ethyl 4-[1-[2- 2,4 -difluorobenzhydryloxy)ethyl]-4-piperidyl}butyrate;

2-154. Ethyl 6-{1-[2-(2,4-difluorobenzhydryloxy)ethyl]-4-piperidyl]hexanoate;

2-179. Propyl 4-[1-[2-bis(4-fluorophenyl)methoxyethyl]-4-piperidyl}butyrate;

2-180. Butyl 4-[1-[2-bis(4-fluorophenyl)methoxyethyl]-4-piperidyl}butyrate;

and salts thereof.

The compounds of the present invention can be prepared by a variety of processes well known in the art for the preparation of compounds of this type. For in general terms, they may be prepared by reacting a compound of formula (II):

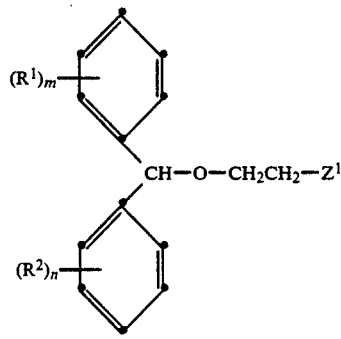

(II)

with a compound of formula (III):

$Z^2$—COOR$^{11}$    (III)

in which:

$R^1$, $R^2$, m and n are as defined above;

$R^{11}$ represents a hydrogen atom or an ester group, such as those represented by $R^3$; and (i) $Z^1$ represents a halogen atom and $Z^2$ represents a group of formula (IV):

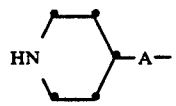

(IV)

OR $Z^1$ represents a group of formula (V):

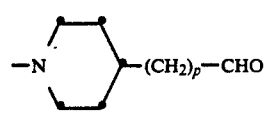

(V)

and $Z^2$ represents a group of formula (VI):

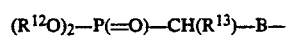

(VI)

OR (iii) $Z^1$ represents a group of formula (VII):

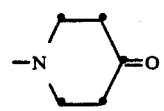

(VII)

and $Z^2$ represents a group of formula (VIII):

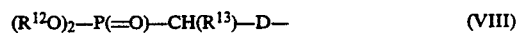

(VIII)

in which:

$R^{12}$ represents an alkyl group having from 1 to 4 carbon atoms;

$R^{13}$ represents a hydrogen atom, an alkyl group having from 1 to 4 carbon atoms or an alkynyl group having 3 or 4 carbon atoms (e.g. a propargyl group or a 2-butynyl group;

B represents a direct carbon-carbon bond, an alkylene group having from 1 to 4 carbon atoms or an alkenylene group having from 2 to 4 carbon atoms;

D represents an alkylene group having from 1 to 7 carbon atoms or an alkenylene group having from 2 to 7 carbon atoms; and p is 0 or an integer of from 1 to 4.

The halogen atom represented by $Z^1$ is preferably a chlorine, bromine or iodine atom.

If desired, any carbon-carbon double and triple bonds in the side chain attached to the piperidine group may then be hydrogenated, and/or, if desired, where $R^{11}$ represents a hydrogen atom, the compound may be esterified, and/or, if desired, where $R^{11}$ represents an ester group, the compound may be hydrolised.

In more detail, the compounds may be prepared as illustrated in the following Reaction Schemes A, B and C:

Reaction Scheme A:

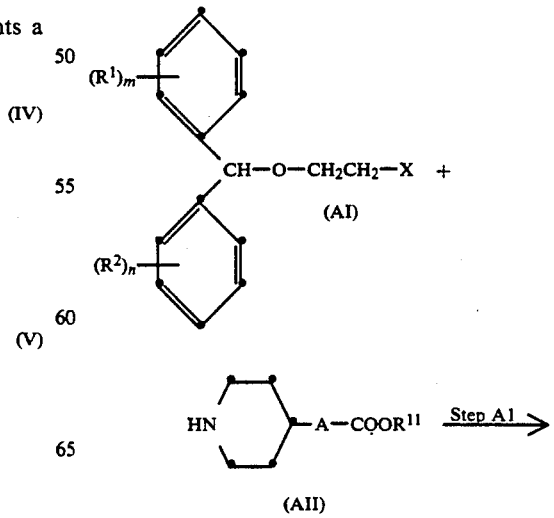

Reaction Scheme A:

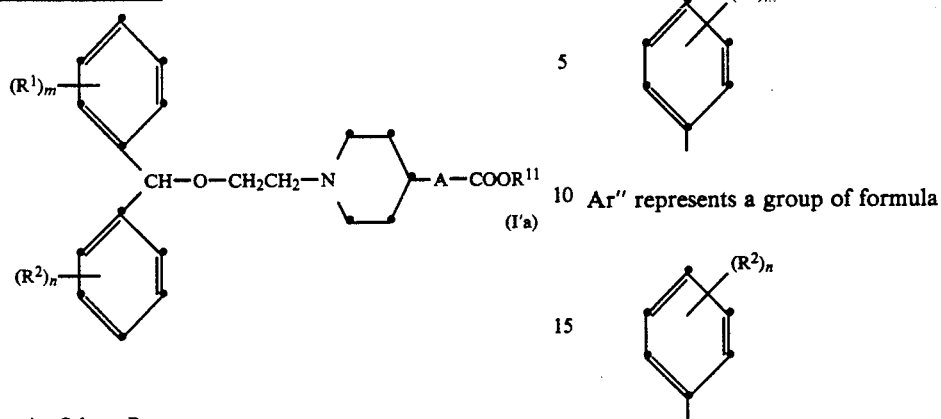

Ar" represents a group of formula

Reaction Scheme B:

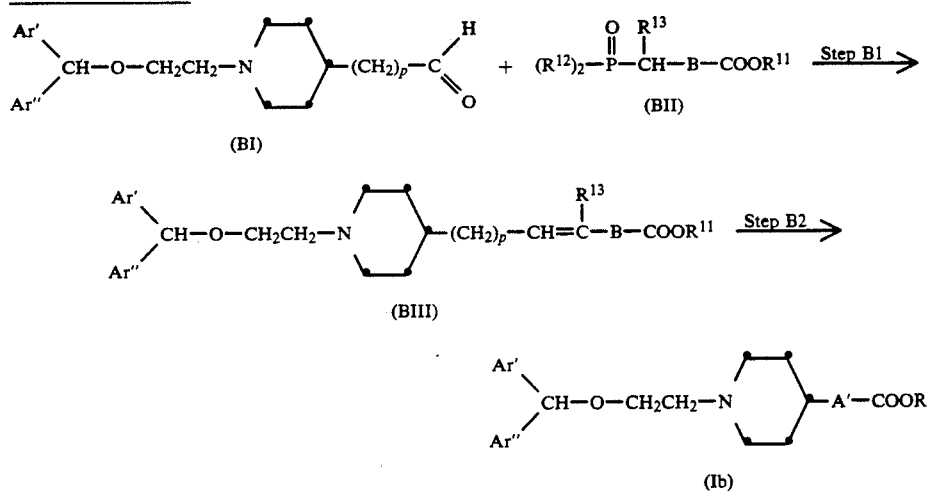

Reaction Scheme C:

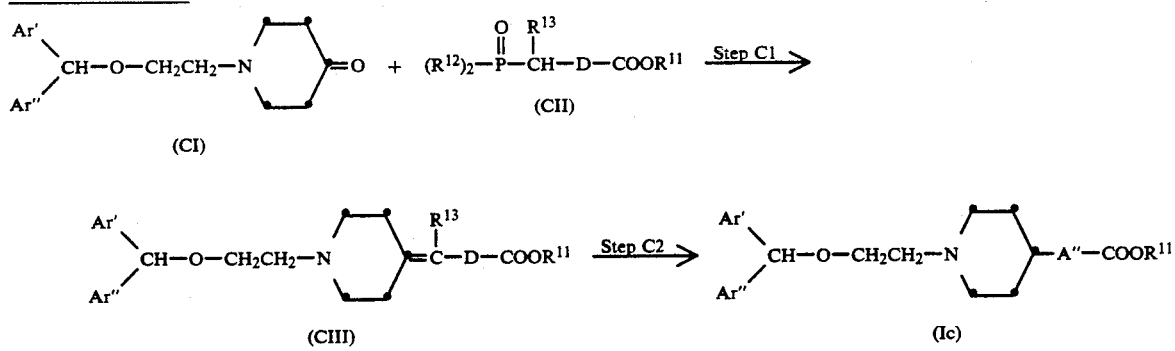

In the above formulae:
R¹, R², m, n, p, A, B, D, R¹¹, R¹² and R¹³ are as defined above;
X represents a halogen atom, preferably a chlorine, bromine or iodine atom;
Ar' represents a group of formula (where R¹, R², m and n are as defined above);
A' represents a group of formula:

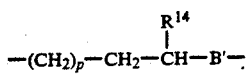

(where p is as defined above; B' represents a direct carbon-carbon bond or an alkylene group having from 1 to 4 carbon atoms; and R¹⁴ represents a hydrogen atom or an alkyl group having from 1 to 4 carbon atoms); and A" represents a group of formula:

(wherein $R^{14}$ is as defined above and D' represents an alkylene group having from 1 to 7 carbon atoms).

In the definition of B and D, each of $C_1$-$C_4$ and $C_1$-$C_7$ alkylene groups may be a methylene group or a higher alkylene group or an alkenylene group containing the corresponding number of carbon atoms to form the group represented by A, and these are preferably a trimethylene, pentamethylene and heptamethylene group or a group of formula —$CH_2CH$=$CH$—, —$(CH_2)_3CH$=$CH$— or —$(CH_2)_5$—$CH$=$CH$—.

In Reaction Scheme A, the compound of formula (I) is prepared by reacting a halogen compound of formula (AI) with a piperidine compound of formula (AII) in the presence of a base in an inert solvent.

There is no particular restriction on the nature of the base to be employed in this reaction, provided that it has no adverse effect on any part of the molecules of the reagents, and any base commonly used in dehydrohalogenation condensation reactions can equally be used here. Examples of bases which may be employed include: alkali metal carbonates, such as sodium carbonate and potassium carbonate; alkali metal hydrogencarbonates, such as sodium hydrogencarbonate and potassium hydrogencarbonate; and organic amines, such as triethylamine, pyridine, 4-dimethylaminopyridine, N-methylmorpholine and DBU (1,8-diazabicyclo[5,4,0]-undec-7-ene). Of these, we prefer the alkali metal carbonates and alkali metal bicarbonates.

There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; alcohols, such as methanol, ethanol or propanol; ketones, such as acetone, methyl ethyl ketone or methyl isobutyl ketone; and amides, especially fatty acid amides, such as dimethylformanide or dimethylacetamide. Of these, we prefer the ketones and amides.

The reaction can take place over a wide range of temperatures, and the precise reaction temperature is not critical to the invention. In general, we find it convenient to carry out the reaction at a temperature of from room temperature to 150° C. (preferably from 80° C. to 120° C.). The time required for the reaction may also vary widely, depending on many factors, notably the reaction temperature and the nature of the reagents. However, provided that the reaction is effected under the preferred conditions outlined above, a period of from 1 to 30 hours (preferably from 3 to 16 hours) will usually suffice.

If desired, those compounds of formula (I'a) wherein $R^{11}$ represents a hydrogen atom, can be prepared by hydrolysis of the corresponding compound in which $R^{11}$ represents an ester group.

The hydrolysis reaction may be carried out by conventional means, for example, by reacting the ester compound with a base (e.g. an alkali metal hydroxide, such as sodium hydroxide or potassium hydroxide, or an alkali metal carbonate, such as sodium carbonate or potassium carbonate) in an inert solvent (e.g. an aqueous alcohol, such as aqueous methanol or aqueous ethanol, or an aqueous ether, such as aqueous tetrahydrofuran or aqueous dioxane) at a suitable temperature, e.g. from room temperature to 100° C. (preferably from room temperature to 80° C.), normally for a period of from 10 minutes to 24 hours (preferably from 20 minutes to 3 hours).

If desired, those compounds of formula (I'a) wherein $R^{11}$ represents an ester group, can be prepared by esterification of the corresponding compound in which $R^{11}$ represents a hydrogen atom with a compound of formula $R^3$—X (in which $R^3$ and X are as defined above). The esterification reaction may be carried out in a similar manner to the reaction of Step A1, using similar reaction conditions, bases and solvents.

The compounds of formula (AI) used as starting materials in this step are well known or can easily be prepared by well known methods [for example, the method described in J. Med. Chem., 23, 149 (1980)].

The reactions of Reaction Scheme B prepare compounds of formula (I) in which A represents either a group of formula

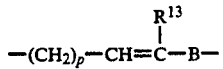

or any of the groups represented by A' (in which $R^{13}$, A', B and p are as defined above), that is to say compounds of formula (BIII) and (Ib).

In Step B1 of Method B, a compound of formula (BIII) is prepared by treating a phosphonate compound of formula (BII) with a base to give a carbanion and then reacting the resulting carbanion with the aldehyde compound of formula (BI).

There is no particular restriction on the nature of the base to be employed in the reaction to produce the carbanion, provided that it has no adverse effect on any part of the molecule of the compound of formula (BI). (BII) or (BIII), and any base capable of generating a carbanion from phosphonate compounds of this type can equally be used here. Examples of bases which may be employed include: alkali metal hydrides, such as lithium hydride or sodium hydride; alkyllithium compounds, such as methyllithium or butyllithium; lithium alkylamides, such as lithium diisopropylamide or lithium dicyclohexylamide; and alkali metal silyl compounds, such as sodium 1,1,1,3,3,3-hexamethyldisilazane or lithium 1,1,1,3,3,3-hexamethyldisilazane. Of these, the alkali metal hydrides are preferred.

There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; and hydrocarbons, preferably aromatic hydrocarbons, such as benzene or toluene. Of these, the ethers are preferred.

The reaction can take place over a wide range of temperatures, and the precise reaction temperature is not critical to the invention. In general, we find it convenient to carry out the reaction for the production of a carbanion at a temperature of from −70° C. to 50° C. (preferably from −20° C. to 10° C.) and that for reacting the carbanion with the compound of formula (BI) at a temperature of from −100° C. to 50° C. (preferably from 0° C. to about room temperature). The time required for the reaction may also vary widely, depending on many factors, notably the reaction temperature and the nature of the reagents. However, provided that the reaction is effected under the preferred conditions outlined above, the time required for the reaction producing a carbanion is usually from 30 minutes to 3 hours and that for the reaction of the carbanion with the compound of formula (BI) is usually from 30 minutes to 6 hours (preferably from 1 to 3 hours).

In the compound of formula (BIII), where $R^{11}$ represents an ester group, the corresponding carboxylic acid derivative of formula (BIII) in which $R^{11}$ represents a hydrogen atom can be prepared by hydrolysis in a similar manner to that described as an optional step at the end of Reaction Scheme A.

The compound of formula (BI) used as the starting material in this step can be prepared by reacting an ester or nitrile compound of formula (IX):

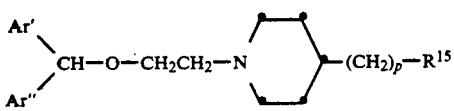
(IX)

[in which Ar', Ar" and p are as defined above and $R^{15}$ represents a group of formula —$COOR^{16}$ (in which $R^{16}$ represents an ester group as in the definition of $R^{11}$) or a nitrile group] with a reducing agent (e.g., an aluminum hydride, such as diisobutylaluminum hydride) in an inert solvent (e.g. an ether, such as tetrahydrofuran) at a suitable temperature, e.g. from −78° C. to room temperature, usually for a period of from 30 minutes to 5 hours.

The compound of formula (IX) can be prepared by reacting the compound of formula (A1) (see Reaction Scheme A) with a compound of formula (IX'):

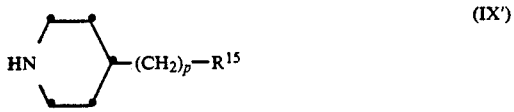
(IX')

(in which p and $R^{15}$ are as defined above) in a similar manner to that described in Step A1 (Reaction Scheme A).

A compound of formula (BI) wherein p is 0 can also be prepared by reacting a compound (CI) (see Reaction Scheme C) with a phosphonate compound of formula (X):

(X)

(wherein $R^{12}$ is as defined above) and reacting the resulting compound with an acid (e.g. a mineral acid, such as hydrochloric acid) in the presence of water at a suitable temperature, e.g. about room temperature, usually for a period of from 30 minutes to 5 hours.

In Step B2 of Reaction Scheme B, a compound of formula (Ib) is prepared by catalytic reduction of the compound of formula (BIII). The reaction can be carried out in an atmosphere of hydrogen and in the presence of a catalyst and of inert solvent.

Any catalyst commonly employed for catalytic hydrogenation may equally be used in this Step, and examples include palladium-on-charcoal, platinum black and rhodium-on-charcoal, of which palladium-on-charcoal is preferred. The hydrogen pressure employed in the reaction is preferably from 1 to 10 times atmospheric pressure (more preferably from 1 to 4 times atmospheric pressure).

There is no particular restriction on the nature of the solvent to be employed, provided that it has no adverse effect on the reaction or on the reagents involved and that it can dissolve the reagents, at least to some extent. Examples of suitable solvents include: alcohols, such as methanol or ethanol; and ethers, such as dioxane or tetrahydrofuran. Of these, the alcohols are preferred.

The reaction can take place over a wide range of temperatures, and the precise reaction temperature is not critical to the invention. In general, we find it convenient to carry out the reaction at a temperature of from 0° C. to 100° C. (preferably 10° C. to 30° C.). The time required for the reaction may also vary widely, depending on many factors, notably the reaction temperature and the nature of the reagents. However, provided that the reaction is effected under the preferred conditions outlined above, a period of from 10 minutes to 10 hours (more preferably from 10 minutes to 3 hours) will usually suffice.

A compound of formula (Ib) wherein $R^{11}$ represents a hydrogen atom can be prepared by hydrolysis of the corresponding compound wherein $R^{11}$ represents an ester group, and a compound of formula (Ib) wherein $R^{11}$ represents an ester group can be prepared by esterification of the corresponding compound in which $R^{11}$ represents a hydrogen atom with a compound of formula $R^3$—X (in which $R^3$ and X are as defined above), each in a similar manner to that described as an optional step in Reaction Scheme A.

In Reaction Scheme C, a compound of formula (I) wherein A represents a group A" (which is as defined above), that is to say a compound (Ic), can be prepared following Steps C1 and C2, which are essentially the same as Steps B1 and B2 of Reaction Scheme B and which may be carried out using the same reaction conditions and reagents.

The compound of formula (CI) employed as the starting material in this Reaction Scheme can be prepared by reacting a compound of formula (XI):

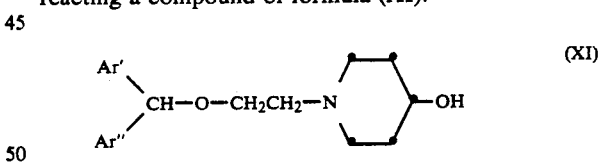
(XI)

(in which Ar' and Ar" are as defined above) with an oxidizing agent (e.g. a mixture of dimethyl sulfoxide and oxalyl chloride) in an inert solvent (e.g. methylene chloride) at a temperature of from −70° C. to −50° C. for a period of from 10 minutes to 1 hour. Alternatively, it may be prepared by reacting a compound of formula (AI), see Reaction Scheme A, with 4-piperidone, under conditions similar to those described for the reaction of the compound of formula (AI) with the compound of formula (AII) in Step A1 of Reaction Scheme A.

After completion of any of the above reactions, the desired product of each step can be recovered from the reaction mixture by conventional means. For example, one suitable recovery technique comprises filtering off insoluble materials, if any (such as a catalyst), from the reaction mixture; and then distilling off the solvent. Alternatively, the solvent may be removed by distillation, after which water is added, and the mixture is extracted with a water-immiscible solvent and the solvent is removed by distillation. Where the desired product is a carboxylic acid derivative or other water-soluble compound, it may be recovered by adding water to the reaction mixture, extracting the mixture with a water-immiscible solvent, acidifying the aqueous layer, e.g. with dilute hydrochloric acid, extracting the mixture with a water-immiscible solvent and finally distilling off the solvent. The desired product can, if necessary, be further purified by such conventional means as recrystallization and/or the various chromatography techniques, notably column chromatography or preparative thin layer chromatography.

The piperidyl-aliphatic acid derivatives of the present invention have, as shown in the following biological activity data, exhibited excellent anti-histamic, anti-allergic and anti-asthmatic activities and an excellent inhibitory activity against the accumulation of eosinophile in the bronchoalveolar lavage fluid. Accordingly, the compounds are useful as therapeutic agents for the treatment or prophylaxis of various histamine-related disorders, especially allergic diseases, such as rhinitis or chronic urticaria, or asthma.

The compounds of the present invention may, therefore, be used in the treatment of such disorders, and, for this purpose, may be formulated as conventional pharmaceutical preparations, as is well known in the art. Thus, the compounds may be administered orally, e.g. in the form of tablets, capsules, granules, powders, syrups, sprays, inhalations or other such well known forms, or parenterally, e.g. by injections, sprays, inhlations, eyedrops, adhesive plasters or suppositories, etc.

These pharmaceutical preparations can be prepared by conventional means and may contain known adjuvants of a type commonly used in this field, for example vehicles, binders, disintegrators, lubricants, stabilizers, corrigents, etc, depending upon the intended use and form of the preparation. The dose will depend upon the condition, age, and body weight of the patient as well as upon the nature and severity of the disorder to be treated, but, in the case of oral administration to an adult human patient, we would normally suggest a total daily dose of from 0.01 mg to 50 mg, which may be administered in a single dose or in divided doses, e.g. from one to three times a day.

The preparation of the compounds of the present invention is further illustrated by the following Examples, and the preparation of certain of the compounds used as starting materials in some of these Examples is illustrated in the subsequent Preparations. The biological activity of certain of the compounds of the present invention is illustrated in the following test examples.

EXAMPLE 1

Ethyl 3-[1-[2-bis(4-fluorophenyl)methoxyethyl]-4-piperidyl-}acrylate and its oxalate and fumarate 1(1) Ethyl 3-{1-[2-bis(4-fluorophenyl]-4-piperidyl}acrylate 0 87 g of sodium hydride (as a 50% w/w dispersion in mineral oil) was added under a stream of nitrogen to 90 ml of anhydrous tetrahydrofuran. 20 ml of an anhydrous tetrahydrofuran solution containing 4.01 g of ethyl diethylphosphonoacetate were then added dropwise to the mixture at 0° C., and the resulting mixture was stirred for 30 minutes at room temperature. 50 ml of an anhydrous tetrahydrofuran solution containing 5.85 g of 1-[2-bis(4-fluorophenyl)methoxyethyl]-4-piperidinecarbaldehyde (prepared as described in preparation 1) were then added dropwise to the reaction mixture at 0° C., and the mixture was stirred for 1 hour at room temperature. At the end of this time, the solvent was removed by distillation under reduced pressure. Ice water was added to the residue, and the mixture was extracted with ethyl acetate. The extract was concentrated by distillation under reduced pressure and purified by silica gel column chromatography. Elution with 5% by volume methanol in methylene chloride afforded 6.34 g (yield: 91%) of the title compound as a yellow oil.

Nuclear Magnetic Resonance Spectrum (CDCl$_3$) δ ppm: 1.27 (3H, triplet; 1.46–2.33 (7H, multiplet); 2.63 (2H, triplet); 2.78–3.07 (2H, multiplet); 3.55 (2H, triplet); 4.18 (2H, quartet); 5.34 (1H, broad singlet); 5.79 (1H, doublet); 6.79–7.45 (9H, multiplet).

Infrared Absorption Spectrum (CHCl$_3$), $\nu_{max}$ cm$^{-1}$; 2920, 1705, 1650, 1600, 1500.

1(2) The oxalate and fumarate

The oxalate and fumarate of the title compound were prepared by dissolving the title compound in ethanol, adding a molar equivalent of the corresponding acid, and collecting the precipitated crystals by filtration, the oxalate melting at 142°–143° C., and the fumarate melting at 154°–156° C.

EXAMPLES 2 to 20

The following compounds were prepared by a procedure similar to that described in Example 1(1), but using the corresponding aldehydes and the corresponding phosphonic acid esters, and then, in some cases, converting the product to the oxalate or fumarate, as described in Example 1(2).

EXAMPLE 2

Methyl 3-{1-[2-bis(4-fluorophenyl)methoxyethyl]-4-piperidyl-}acrylate oxalate

This was obtained in a yield of 62%, as crystals melting at 135°–136° C.

EXAMPLE 3

Methyl 3-{I-(2-benzhydryloxyethyl)-4-piperidyl}acrylate oxalate

This was obtained in a yield of 42%, as crystals melting at 134°–136° C.

EXAMPLE 4

Ethyl 3-{1-(2-benzhydryloxyethyl)-4-piperidyl}acrylate oxalate

This was obtained in a yield of 48%, as crystals melting at 145°–147° C.

EXAMPLE 5

Methyl 3-{1-2-(4-chlorobenzhydryloxy)ethyl]-4-piperidyl}acrylate oxalate

This was obtained in a yield of 100%, as crystals melting at 158°–160° C.

EXAMPLE 6

Ethyl 3-{1-[2-(4-chlorobenzhydryloxy)ethyl]-4-piperidyl}acrylate oxalate

This was obtained in a yield of 100%, as crystals melting at 148°–150° C.

EXAMPLE 7

Ethyl 3-{1-2-bis(4-fluorophenyl)methoxyethyl]-4-piperidyl} methacrylate and its fumarate This was obtained in a quantitative yield.
Infrared Absorption Spectrum (CHCl$_3$), $\nu_{max}$ cm$^{-1}$: 2910, 1695, 1600, 1500.
The fumarate, melting at 108°–110° C., was then prepared.

EXAMPLE 8

Ethyl 3-{1-[2-bis(4-fluorophenyl)methoxyethyl]-4-piperidyl}-2-propargylacrylate and its fumarate This was obtained in a yield of 54%.
Infrared Absorption Spectrum (CHCl$_3$), $\nu_{max}$ cm$^{-1}$: 2910, 1940, 1705, 1600, 1500.
The fumarate, melting at 81°–83° C., was then prepared.

EXAMPLE 9

Ethyl 5-{1-2-bis(4-fluorophenyl)methoxyethyl]-4-piperidyl}-2,4-pentadienoate and its oxalate This was obtained in a yield of 81%.
Infrared Absorption Spectrum (CHCl$_3$), $\nu_{max}$ cm$^{-1}$: 2950, 1705, 1645, 1610, 1510.
The oxalate, melting at 137°–140° C., was then prepared.

EXAMPLE 10

Ethyl 5-{1-2-bis(4-fluorophenyl)methoxyethyl]-4-piperidyl}-2-pentenoate and its oxalate This was obtained in a yield of 84%.
Infrared Absorption Spectrum (CHCl$_3$), $\nu_{max}$ cm$^{-1}$: 2925, 1705, 1650, 1605, 1505.
The oxalate, melting at 136°–138° C., was then prepared.

EXAMPLE 11

Ethyl 5-{1-[2-bis(4-fluorophenyl)methoxyethyl-4-piperidyl}-2-methyl-2-pentenoate and its oxalate This was obtained in a yield of 98%.
Infrared Absorption Spectrum (CHCl$_3$), $\nu_{max}$ cm$^{-1}$: 2925, 1700, 1605, 1510.
The oxalate, melting at 152°–153° C., was then prepared.

EXAMPLE 12

Ethyl 6-{1-[2-bis(4-fluorophenyl)methoxyethyl]-4-piperidyl}-2-hexenoate and its fumarate This was obtained in a yield of 72%.
Infrared Absorption Spectrum CHCl$_3$), $\nu_{max}$ cm$^{-1}$: 2900, 1705, 1650, 1600.
The fumarate, melting at 132°–133° C., was then prepared.

EXAMPLE 13

Ethyl 6-{1-[2-bis(4-fluorophenyl)methoxyethyl]-4-piperidyl}-2-methyl-2-hexenoate This was obtained in a yield of 88%.
Infrared Absorption Spectrum (CHCl$_3$), $\nu_{max}$ cm$^{-1}$: 2910, 1695, 1645, 1600, 1505.

EXAMPLE 14

Ethyl 8-{1-[2-bis(4-fluorophenyl)methoxyethyl]-4-piperidyl}-2,4-octadienoate

This was obtained in a yield of 84%.
Infrared Absorption Spectrum (CHCl$_3$), $\nu_{max}$ cm$^{-1}$: 2900, 1695, 1635, 1600, 1500.

EXAMPLE 15

Ethyl 7-{1-[2-bis(4-fluorophenyl)methoxyethyl]-4-piperidyl}-2-heptenoate

This was obtained in a yield of 34%.
Infrared Absorption Spectrum (CHCl$_3$), $\nu_{max}$ cm$^{-1}$: 2950, 1715, 1655, 1610, 1510.

EXAMPLE 16

Ethyl 4-[1-(2-benzhydryloxyethyl)-4-piperidyl]-2-butenoate

This was obtained in a yield of 71%.
Infrared Absorption Spectrum (CHCl$_3$), $\nu_{max}$ cm$^{-1}$: 2925, 1710, 1645, 1600, 1510.

EXAMPLE 17

Ethyl 4-{1-[2-(4-chlorobenzhydryloxy)ethyl]-4-piperidyl}-2-butenoate

This was obtained in a yield of 95%.
Infrared Absorption Spectrum (CHCl$_3$), $\nu_{max}$ cm$^{-1}$: 2930, 1710, 1655, 1600, 1490.

EXAMPLE 18

Ethyl 4-{1-[2-(4-fluorobenzhydryloxy)ethyl]-4-piperidyl}-2-butenoate

This was obtained in a yield of 71%.
Infrared Absorption Spectrum CHCl$_3$), $\nu_{max}$ cm$^{-1}$: 2930, 1710, 1645, 1605, 1510.

EXAMPLE 19

Ethyl 4-{1-[2-(4-methylbenzhydryloxy)ethyl]-4-piperidyl}-2-butenoate

This was obtained in a yield of 95%.
Infrared Absorption Spectrum CHCl$_3$), $\nu_{max}$ cm$^{-1}$: 2925, 1710, 1645, 1605, 1510.

EXAMPLE 20

Ethyl 4-{1-[2-bis(4-fluorophenyl)methoxyethyl]-4-piperidyl}-2-butenoate

This was obtained in a yield of 91%.

Infrared Absorption Spectrum (CHCl₃), $v_{max}$ cm⁻¹: 2930, 1710, 1655, 1605, 1510.

EXAMPLE 21

Ethyl 3-{1-[2-bis(4-fluorophenyl)methoxyethyl]-4-piperidyl} propionate 0.14 g of 10% w/w palladium-on-charcoal and 1.569 g of ethyl 3-{1-[2-bis(4-fluorophenyl)methoxyethyl]-4-piperidyl}acrylate (prepared as described in Example 1) were added to 30 ml of ethanol, and the mixture was stirred in an atmosphere of hydrogen at room temperature for 30 minutes. At the end of this time, the catalyst was removed by filtration, and the filtrate was freed from the solvent by distillation under reduced pressure, to afford 1.46 g (93% yield) of the title compound as a yellow oil.

Infrared Absorption Spectrum (CHCl₃), $v_{max}$ cm⁻¹: 2920, 1725, 1600, 1505.

EXAMPLES 22 TO 34

The following compounds were prepared by using the reduction reaction described in Example 21 from the corresponding unsaturated starting materials (which themselves were prepared as in the corresponding ones of Examples 2 to 20), and, in some cases, this was followed by salification, as described in Example 1(2).

EXAMPLE 22

Ethyl 3-{1-2-bis(4-fluorophenyl)methoxyethyl]-4-piperidyl}-2-methylpropionate and its oxalate This was obtained in a yield of 92%.

Infrared Absorption Spectrum (CHCl₃), $v_{max}$ cm⁻¹: 2900, 1720, 1600, 1500.

The oxalate, melting at 130°-131° C. (with decomposition), was then prepared.

EXAMPLE 23

Ethyl 3-{1-2-bis(4-fluorophenyl)methoxyethyl]-4-piperidyl}-2-propylpropionate and its oxalate This was obtained in a yield of 67%.

Infrared Absorption Spectrum (CHCl₃), $v_{max}$ cm⁻¹: 2950, 1725, 1610, 1510.

The oxalate, melting at 134°-137° C., was then prepared.

EXAMPLE 24

Ethyl 5-{1-2-bis(4-fluorophenyl)methoxyethyl]-4-piperidyl} valerate and its oxalate This was obtained in a yield of 85%.

Infrared Absorption Spectrum (CHCl₃), $v_{max}$ cm⁻¹: 2925, 1725, 1605, 1505.

The oxalate, melting at 134°-135° C., was then prepared.

EXAMPLE 25

Ethyl 6-{1-[2-bis(4-fluorophenyl)methoxyethyl]-4-piperidyl} hexanoate and its oxalate This was obtained in a yield of 81%.

Infrared Absorption Spectrum (CHCl₃), $v_{max}$ cm⁻¹: 2940, 1730, 1605, 1510.

The oxalate, melting at 130°-131° C., was then prepared.

EXAMPLE 26

Ethyl 6-{1-[2-bis(4-fluorophenyl)methoxyethyl]-4-piperidyl}-2-methylhexanoate and its oxalate This was obtained in a yield of 77%.

Infrared Absorption Spectrum (CHCl₃), $v_{max}$ 2950, 2875, 1725, 1610, 1510.

The oxalate, melting at 137°-138° C., was then prepared.

EXAMPLE 27

Ethyl 8-{1-[2-bis(4-fluorophenyl)methoxyethyl]-4-piperidyl}octanoate and its oxalate This was obtained in a yield of 79%.

Infrared Absorption Spectrum (CHCl₃), $v_{max}$ cm⁻¹: 2940, 2875, 1730, 1605, 1510.

The oxalate, melting at 119°-120° C., was then prepared.

EXAMPLE 28

Ethyl 7-{1-[2-bis(4-fluorophenyl)methoxyethyl]-4-piperidyl} heptanoate and its oxalate This was obtained in a yield of 42%.

Infrared Absorption Spectrum (CHCl₃), $v_{max}$ cm⁻¹: 2950, 2875, 1730, 1610, 1510.

The oxalate, melting at 120°-121° C. was then prepared.

EXAMPLE 29

Ethyl 5-{1-[2-bis(4-fluorophenyl)methoxyethyl]-4-piperidyl}-2-methylvalerate and its oxalate This was obtained in a yield of 81%.

Infrared Absorption Spectrum (CHCl₃), $v_{max}$ cm⁻¹: 2940, 1725, 1605, 1505.

The same compound, having the same Infrared Spectrum, was also prepared using the reduction reaction described in Example 21 from ethyl 4-{4-[2-bis(4-fluorophenyl)methoxyethyl]piperidylidene}butenoate (prepared as described in preparation 19) in a yield of 90%.

The oxalate, melting at 138°-140° C., was then prepared.

EXAMPLE 30

Ethyl 4-[1-(2-benzhydryloxyethyl)-4-piperidyl]butyrate

This was obtained in a quantitative yield.

Infrared Absorption Spectrum (CHCl₃), $v_{max}$ cm⁻¹: 2925, 1725, 1600, 1495.

The oxalate, melting at 103°-104° C., Was then prepared.

EXAMPLE 31

Ethyl 4-{1-[2-(4-chlorobenzhydryloxy)ethyl]-4-piperidyl}butyrate

This was obtained in a yield of 96%.

Infrared Absorption Spectrum (CHCl₃), $v_{max}$ cm⁻¹: 2975, 1730, 1605, 1455.

The oxalate, melting at 117°–119° C., was then prepared.

EXAMPLE 32

Ethyl 4-{1-[2-(4-fluorobenzhydryloxy)ethyl]-4-piperidyl}butyrate

This was obtained in a quantitative yield.

Infrared Absorption Spectrum (CHCl$_3$), $\nu_{max}$ cm$^{-1}$: 2930, 1725, 1605, 1510.

The oxalate, melting at 119°–120° C., was then prepared.

EXAMPLE 33

Ethyl 4-{1-2-(4-methylbenzhydryloxy)ethyl]-4-piperidyl}butyrate

This was obtained in a quantitative yield.

Infrared Absorption Spectrum (CHCl$_3$), $\nu_{max}$ cm$^{-1}$: 2930, 1730, 1600, 1505.

The oxalate, melting at 114°–115° C., was then prepared.

EXAMPLE 34

Ethyl 4-{1-2-bis(4-fluorophenyl)methoxyethyl]-4-piperidyl} butyrate and its oxalate This was obtained in a yield of 87%.

Infrared Absorption Spectrum CHCl$_3$), $\nu_{max}$ cm$^{-1}$: 2940, 1730, 1610, 1510.

The oxalate, melting at 143°–145° C., was then prepared.

EXAMPLE 35

Ethyl 4-{1-2-bis(4-chlorophenyl)methoxyethyl-4-piperidyl} butyrate 0.68 g of 1-bis(4-chlorophenyl)methoxy-2-chloroethane, 0.43 g of ethyl 4-(4-piperidyl)butyrate (prepared as described in preparation 20), 1.8 g of sodium carbonate and 0.05 g of sodium iodide were added to 60 ml of methyl isobutyl ketone, and the mixture was heated under reflux for 16 hours. At the end of this time, the mixture was filtered, and the filtrate was concentrated by distillation under reduced pressure. The resulting residue was subjected to column chromatography through silica gel using ethyl acetate as the eluent, to afford 1.0 g (97% yield) of the title compound as a pale yellow oil.

Infrared Absorption Spectrum CHCl$_3$), $\nu_{max}$ cm$^{-1}$: 2925, 1730, 1600, 1495.

Following the procedure described in Example 1(2), the oxalate of the title compound, melting at 131°–132° C., was prepared.

EXAMPLE 36

4-{1-[2-bis(4-Fluorophenyl)methoxyethyl]-4-piperidyl}-butyric acid 1.64 g of ethyl 4-{1-[2-bis(4-fluorophenyl)methoxyethyl]-4-piperidyl}butyrate (prepared as described in Example 34) were added to 15 ml of ethanol, and then 10 ml of a 10% w/v aqueous solution of sodium hydroxide were added, and the mixture was stirred at room temperature for 2 hours. The reaction mixture was then concentrated by evaporation under reduced pressure, and the resulting residue was diluted with water. The pH was then adjusted to a value of 4 by the addition of aqueous hydrochloric acid, and then the mixture was extracted with ethyl acetate. The crystals obtained from the extract were recrystallized from ethanol to afford 1.46 g (95% yield) of the title compound, melting at 145°–147° C.

Infrared Absorption Spectrum (KBr), $\nu_{max}$ cm$^{-1}$: 2938, 2873, 2700, 1720, 1603, 1507, 1223.

EXAMPLE 37

Butyl 4-{1-2-bis(4-fluorophenyl)methoxyethyl]-4-piperidyl} butyrate 2 ml of butanol and 0.10 g of sodium hydride (as a 55% w/w dispersion in mineral oil) were added to a solution of 0.80 g of ethyl 4-[1-[2-bis(4-fluorophenyl)-methoxyethyl]-4-piperidyl}butyrate (prepared as described in Example 34) in 20 ml of toluene at room temperature, and the mixture was stirred whilst heating under reflux for 5 hours. At the end of this time, the mixture was cooled to room temperature, and then ice-water was poured into the mixture and the mixture was extracted with ethyl acetate. The extracts were washed with water and dried over anhydrous sodium sulfate. The solvent was then removed by evaporation under reduced pressure. The resulting residue was purified by column chromatography through silica gel, using ethyl acetate as the eluent, to give 0.38 g of the title compound as a yellow oil.

Infrared Absorption Spectrum (CHCl$_3$), $\nu_{max}$ cm$^{-1}$: 2930, 1725, 1605, 1508.

Following the procedure described in Example 1(2), the oxalate of the title compound, melting at 28°–130° C., was prepared.

PREPARATION 1

1-[2-Bis(4-fluorophenyl)methoxyethyl]-4-piperidinecarbaldehyde

This preparation describes three methods of making the same title compound.

1(a) 75 ml of a 1M hexane solution containing diisobutylaluminum hydride were added to 400 ml of tetrahydrofuran under a stream of nitrogen, and the mixture was cooled at −78° C. Whilst the mixture's internal temperature was −15° C., 20.25 g of 1-[2-bis(4-fluorophenyl)methoxyethyl]-4-piperidinecarbonitrile (prepared as described in Preparation 4) were added to the mixture over a period of 40 minutes, and the resulting mixture was stirred for 30 minutes at −15° C. The mixture was then allowed to stand overnight at room temperature. At the end of this time, the mixture was placed in an ice bath, and 15 ml of methanol, followed by 100 ml of a saturated aqueous solution of ammonium chloride, were added. The reaction mixture was then extracted with ethyl acetate. The extract was purified by silica gel column chromatography. Elution with 3% by volume methanol in methylene chloride afforded 14.67 g (yield 72%) of the title compound as an oily substance.

Infrared Absorption Spectrum (CHCl$_3$), $\nu_{max}$ cm$^{-1}$: 2930, 2820, 1895, 1725, 1605, 1505.

Nuclear Magnetic Resonance Spectrum CDCl$_3$), δ ppm: 1.40–3.07 (9H, multiplet); 2.63 (2H, triplet); 3.53 (2H, triplet); 5.32 (1H, singlet); 6.82–7.50 8H, multiplet); 9.70 (1H, singlet)

1(b)

420 mg of 1-[2-bis(4-fluorophenyl)methoxyethyl]-4-methoxymethylidenepiperidine (prepared as described in Preparation 5) were added to a mixture of 1.5 ml of 10% w/v aqueous hydrochloric acid and 3 ml of tetrahydrofuran, and the resulting mixture Was then stirred for 2 hours at room temperature. At the end of this time, water was added to the reaction mixture, and it was neutralized by the addition of a 5% w/v aqueous solution of sodium hydroxide and extracted with ethyl acetate. The extract was purified by silica gel column chromatography. Elution with 3% by volume methanol in methylene chloride afforded 434 mg (a quantitative yield) of the title compound as an oil, whose properties were the same as those of the product of step (a).

1(c)

3.03 g of ethyl 1-[2-bis(4-fluorophenyl)methoxyethyl]-4-piperidinecarboxylate (prepared as described in preparation 8) were dissolved in 30 ml of toluene, under a stream of nitrogen, and the resulting solution was cooled at −68° C. 8.2 ml of a 1M solution of diisobutylaluminum hydride in hexane was then added dropwise to the cooled mixture over a period of 10 minutes, and the mixture was stirred for 1 hour at −68° C. At the end of this time, 2 ml of methanol and 3 ml of a saturated aqueous solution of ammonium chloride were added to the reaction solution. The mixture was then extracted with ethyl acetate, to give 2.47 g (yield 91%) of the title compound as an oil, whose properties were the same as those of the product of step (a).

PREPARATIONS 2 AND 3

A procedure similar to that described in Preparation 1 was repeated, except that the appropriate starting materials were used, to give the compounds shown below.

PREPARATION 2

1-(2-Benzhydryloxyethyl)-4-piperidinecarbaldehyde

This was obtained in a yield of 51%.

Nuclear Magnetic Resonance Spectrum (CDCl$_3$), $\delta$ ppm: 2.67 (2H, triplet); 3.59 (2H, triplet); 5.37 (1H, singlet); 9.64 (1H, singlet).

PREPARATION 3

1-[2-(4-Chlorobenzhydryloxy)ethyl]-4-piperidinecarbaldehyde

This was obtained in a yield of 49%.

Nuclear Magnetic Resonance Spectrum (CDCl$_3$), $\delta$ ppm:
2.66 (2H. triplet):
3.57 (2H, triplet);
5.34 (1H, singlet);
9.64 (1H, singlet).

PREPARATION 4

1-[2-Bis(4-fluorophenyl)methoxyethyl]-4-piperidinecarbonitrile 2.13 g of 1-bis(4-fluorophenyl)methoxy-2-chloroethane and 0.95 g of 4-cyanopiperidine were dissolved in 15 ml of dimethylformamide. After this, 4.00 g of anhydrous sodium carbonate and 0.08 g of sodium iodide were added to the resulting solution, and the mixture was stirred for 4 hours at 130° C. At the end of this time, the mixture was poured into ice water and extracted with ethyl acetate. The oily extract obtained was purified by silica gel chromatography. Elution with a 2:1 by volume mixture of ethyl acetate and hexane afforded 2.36 g (yield 88%) of the title compound.

Infrared Absorption Spectrum (CHCl$_3$), $\nu_{max}$ cm$^{-1}$: 2950, 2240, 1670, 1605, 1510.

Nuclear Magnetic Resonance Spectrum (CDCl$_3$), $\delta$ ppm: 1.73–2.08 (4H, multiplet); 2.24–2.97 (5H, multiplet); 2.66 (2H, triplet); 3.54 (2H, triplet); 5.33 (1H, singlet); 6.89–7.45 (8H, multiplet).

PREPARATION 5

1-[2-Bis(4-fluorophenyl)methoxyethyl]-4-methoxymethylidenepiperidine

Under a stream of nitrogen, 2.7 ml of a 1.6M hexane solution of butyllithium were dropped into 440 ml of diisopropylamine in solution in 10 ml of tetrahydrofuran at −78° C. to prepare a solution of lithium diisopropylamide.

Meanwhile, 1.066 g of methoxymethyltriphenylphosphonium chloride was added to 7 ml of tetrahydrofuran, and the mixture was cooled at −10° C. The lithium diisopropylamide solution previously prepared was then added to this mixture, which was then stirred for 30 minutes at −10° C. At the end of this time, 5 ml of a tetrahydrofuran solution containing 1.01 g of 1-[2-bis(4-fluorophenyl)methoxyethyl]-4-piperidone (prepared as described in preparation 6) were dropped into the reaction mixture, at −10° C. The mixture was stirred for 30 minutes, allowed to stand overnight at room temperature, and then condensed by evaporation under reduced pressure. Water was added to the residue, which was then extracted with ethyl acetate. The oily substance obtained was purified by silica gel column chromatography. Elution with a 2:1 by volume mixture of ethyl acetate and hexane afforded 718 mg (yield 66%) of a yellow oily substance.

Infrared Absorption Spectrum (CHCl$_3$), $\nu_{max}$ 2940, 1710, 1690, 1605, 1505.

Nuclear Magnetic Resonance Spectrum (CDCl$_3$), $\delta$ ppm:
1.93–2.87 (10H, multiplet); 3.14–3.70 (2H, multiplet); 3.54 (3H, singlet); 5.35 (1H, singlet); 5.79 (1H, broad singlet); 6.89–7.44 (8H, multiplet).

PREPARATION 6

1-2-Bis(4-fluorophenyl)methoxyethyl]-4-piperidone

This preparation provides two methods of preparing the same title compound.

6(a)

13.33 g of 1-bis(4-fluorophenyl)methoxy-2-chloroethane and 9.22 g of 4-piperidone hydrochloride were dissolved in 270 ml of dimethylformamide, and 14.5 g of anhydrous sodium carbonate and 0.5 g of sodium iodide were added to the resulting solution, which was then stirred for 20 hours at 95° C. At the end of this time, the reaction mixture was poured in ice water and extracted with benzene. The benzene solution was extracted with 5% w/v aqueous hydrochloric acid. Sufficient of a 10% w/v aqueous solution of sodium hydroxide was added to the aqueous layer to make it alkaline, and the mixture was extracted with benzene. The oily substance obtained from the benzene extract was purified by silica gel column chromatography. Elution with a 2% by volume mixture of ethanol and chloroform afforded 6.86 g (yield 42%) of the title compound as a pale yellow oily substance.

Nuclear Magnetic Resonance Spectrum (CDCl$_3$), $\delta$ ppm: 2.43 (4H, triplet); 2.80 (6H, multiplet); 3.60 (2H, triplet); 5.35 (1H, singlet); 7.02 (4H, triplet); 7.28 (4H, doublet of doublets).

Infrared Absorption Spectrum (CHCl₃), $\nu_{max}$ cm⁻¹: 2960, 2800, 1710, 1605, 1505.

6(b)

6.63 ml of oxalyl chloride were dissolved in 160 ml of methylene chloride, and the solution was cooled at −60° C. Whilst the solution was at this temperature, 36 ml of a methylene chloride solution containing 11.3 ml of dimethylsulfoxide were added to it. 160 ml of a methylene chloride solution containing 11.5 g of 1-[2-bis(4-fluorophenyl)methoxyethyl]-4-piperidinol (prepared as described in Preparation 7) were then added to the solution at −60° C., and the resulting mixture was stirred for 15 minutes. At the end of this time, 46 ml of triethylamine were added to the reaction solution. The reaction mixture was then allowed to warm to room temperature, and water was added to it. The aqueous layer was extracted with methylene chloride, and the organic extract was washed with a saturated aqueous solution of sodium chloride. The solvent was then removed by distillation under reduced pressure. The resulting residue was purified by silica gel column chromatography. Elution with a 10:1 by volume mixture of ethyl acetate and methylene chloride afforded 10.23 g (yield 91%) of the title compound as a pale yellow oily substance, whose properties were the same as those of the product of step (a) above.

PREPARATION 7

1-[2-Bis(4-fluorophenyl)methoxyethyl)-4-piperidinol 14.1 g of 1-bis(4-fluorophenyl)methoxy-2-chloroethane, 10.1 g of 4-hydroxypiperidine, 12 g of sodium carbonate and 0.2 g of sodium iodide were added to 200 ml of methyl isobutyl ketone, and the mixture was heated under reflux for 4 hours. At the end of this time, it was filtered, and the solvent was removed by distillation under reduced pressure. The resulting residue was purified by silica gel column chromatography. Elution with a 10:1 by volume mixture of ethanol and methylene chloride afforded 11.5 g (yield 66%) of the title compound as a pale yellow oily substance. p Infrared Absorption Spectrum (CHCl₃), $\nu_{max}$ cm⁻¹: 2920, 1600, 1505.

Nuclear Magnetic Resonance Spectrum (CDCl₃), δ ppm: 1.73 (4H, multiplet); 2.25 (2H, triplet of doublets); 2.65 (2H, triplet); 2.88 (2H, triplet); 3.58 (2H, triplet); 3.69 (1H, multiplet); 5.36 (1H, singlet); 7.01 (4H, triplet); 7.30 (4H, doublet of doublets).

PREPARATION 8

Ethyl 1-[2-bis(4-fluorophenyl)methoxyethyl]-4-piperidinecarboxylate 1.43 g of 1-bis(4-fluorophenyl)methoxy-2-chloroethane and 1.00 g of ethyl isonipecotate were added to 10 ml of methyl isobutyl ketone, and the reaction mixture was then heated under reflux for 5 hours together with 2.0 g of sodium carbonate and 10 mg of potassium iodide. At the end of this time, the mixture was filtered and the solvent was removed by distillation under reduced pressure. The resulting residue was purified by silica gel column chromatography. Elution with a 3:1 by volume mixture of hexane and ethyl acetate afforded 1.45 g (yield 71%) of the title compound as an oily substance.

Infrared Absorption Spectrum (CHCl₃), $\nu_{max}$ 2940, 1725, 1600, 1500.

Nuclear Magnetic Resonance Spectrum (CDCl₃), δ ppm 1.25 (3H, triplet); 1.7-2.5 (7H, multiplet); 2.62 (2H, triplet); 2.88 (2H, multiplet); 3.57 (2H, triplet); 4.13 (2H, quartet); 5.36 (1H, singlet); 7.00 (4H, triplet); 7.28 (4H, doublet of doublets).

PREPARATIONS 9 TO 11

A procedure similar to that described in Preparation was repeated, except that the starting materials used were the esters described in Examples 21, 34 and 24.

PREPARATION 9

3-{1-[2-Bis(4-fluorophenyl)methoxyethyl]-4-piperidyl} propionaldehyde

This was obtained in a yield of 80%.

Infrared Absorption Spectrum CHCl₃), $\nu_{max}$ cm⁻¹: 2940, 1725, 1605, 1510.

PREPARATION 10

4-{1-[2-Bis(4-fluorophenyl)methoxyethyl]-4-piperidyl}-butyraldehyde

This was obtained in a yield of 74%.

Infrared Absorption Spectrum (CHCl₃), $\nu_{max}$ cm⁻¹: 2900, 1715, 1600, 1500.

PREPARATION 11

5-{1-[2-Bis(4-fluorophenyl)methoxyethyl1-4-piperidyl} pentanal

This was obtained in a yield of 76%.

Infrared Absorption Spectrum CHCl₃), $\nu_{max}$ cm⁻¹: 2925, 1720, 1605, 1505.

PREPARATIONS 12 TO 16

A procedure similar to that described in preparation (c) was repeated, except that the corresponding piperidyl-acetic acid derivative was used, to prepare the following compounds.

PREPARATION 12

2-[1-(2-Benzhydryloxyethyl)-4-piperidyl]acetaldehyde

This was obtained in a yield of 55%.

Infrared Absorption Spectrum (CHCl₃), $\nu_{max}$ cm⁻¹: 2930, 2830, 1725, 1605, 1490.

PREPARATION 13

2-{1-[2-(4-Chlorobenzhydryloxy)ethyl]-4-piperidyl}acetaldehyde

This was obtained in a yield of 79%.

Infrared Absorption Spectrum (CHCl₃), $\nu_{max}$ cm⁻¹: 2930, 2830, 1725, 1605, 1495.

PREPARATION 14

2-{1-[2-(4-Fluorobenzhydryloxy)ethyl]-4-piperidyl}acetaldehyde

This was obtained in a yield of 87%.

Infrared Absorption Spectrum (CHCl₃), $\nu_{max}$ cm⁻¹: 2920, 2830, 1725, 1605, 1510.

PREPARATION 15

2-{1-[2-(4-Methylbenzhydryloxy)ethyl]-4-piperidyl}acetaldehyde

This was obtained in a yield of 73%.

Infrared Absorption Spectrum (CHCl$_3$), $\nu_{max}$ cm$^{-1}$:
2930, 1830, 1725, 1605, 1515.

PREPARATION 16

2-{1-[2-Bis(4-fluorophenyl)methoxyethyl]-4-piperidyl-}acetaldehyde

This was obtained in a yield of 32%.

Infrared Absorption Spectrum (CHCl$_3$), $\nu_{max}$ cm$^{-1}$:
2920, 2820, 1725, 1605, 1510.

PREPARATIONS 17 AND 18

Following a procedure similar to that described in Preparation 8, the following compounds were prepared by reacting the corresponding 1-(diphenylmethoxy)-2-chloroethane and ethyl piperidinylacetate compounds.

PREPARATION 17

Ethyl 2-{1-[2-(4-fluorobenzhydryloxy)ethyl]-4-piperidyl}acetate

This was obtained in a yield of 52%.

Infrared Absorption Spectrum (CHCl$_3$), $\nu_{max}$ cm$^{-1}$:
2925, 2800, 1725, 1605, 1500.

PREPARATION 18

Ethyl 2-{(1-[2-bis(4-Fluorophenyl)methoxyethyl]-4-piperidyl-}acetate

This was obtained in a yield of 65%.

Infrared Absorption Spectrum (CHCl$_3$), $\nu_{max}$ cm$^{-1}$:
2925, 2800, 1730, 1605, 1510.

PREPARATION 19

Ethyl 4-{4-[2-bis(4-fluorophenyl)methoxyethyl]-piperidylidene}-2-butenoate

Following the procedure described in Example 1(1), but using 1-[2-bis(4-fluorophenyl)methoxyethyl]-4-piperidone (prepared as described in Preparation 6) and ethyl diethylphosphonocrotonate, the title compound was obtained in a yield of 90%.

Infrared Absorption Spectrum (CHCl$_3$), $\nu_{max}$ cm$^{-1}$:
2940, 2800, 1700, 1635, 1605, 1500.

PREPARATION 20

Ethyl 4-(4-piperidyl)butyrate

20(a) Ethyl 4-[1-benzyl-4-piperidylidene]-2-butenoate

Under an atmosphere of nitrogen, 0.583 g of sodium hydride (as a 50% w/w dispersion in mineral oil) were added to a 4 ml of tetrahydrofuran and the mixture was cooled with water. A solution of 3.04 g of ethyl 4-(diethylphosphono)crotonate in 5 ml of tetrahydrofuran was added dropwise to the cooled mixture, which was then stirred for 30 minutes. At the end of this time, a solution of 1.84 g of 1-benzyl-4-piperidone in 2 ml of tetrahydrofuran was added to the mixture over a period of 30 minutes, whilst the mixture was kept at 0° C. by ice-cooling, and the mixture was stirred at 0° C. for 1 hour. The reaction mixture was then stirred at room temperature for 2 hours, after which it was concentrated by evaporation under reduced pressure. The residue was extracted with ethyl acetate, and the extract was washed with water. The solvent was then removed by distillation under reduced pressure. The red brown residue was subjected to column chromatography through silica gel, using a 5:1 by volume mixture of hexane and ethyl acetate as the eluent, to afford 0.81 g (29% yield) of the title compound as a pale yellow oil.

Infrared Absorption Spectrum (CHCl$_3$), $\nu_{max}$ cm$^{-1}$:
2950, 2800, 1700, 1640, 1610.

20(b) Ethyl 4-(4-piperidyl)butyrate

A solution of 1.60 g of ethyl 4-(1-benzyl-4-piperidylidene)-2-butyrate [prepared as described in step (a) above] in 30 ml of ethanol was stirred at room temperature in the presence of 0.8 g of a 10% w/w palladium-on-charcoal catalyst under 4 atmospheres pressure of hydrogen for 2 hours. At the end of this time, the catalyst was removed from the mixture by filtration, and the solvent was removed by distillation under reduced pressure, to afford 0.7 g (63% yield) of the title compound as a colorless oil boiling at 140° C./6 mmHg.

Infrared Absorption Spectrum (CHCl$_3$), $\nu_{max}$ cm$^{-1}$:
2920, 1725.

TEST EXAMPLE 1

Inhibitory Effect on Passive Cutaneous Anaphylaxis (PCA) in Rats

According to Mota's method [I. Mota, Immunology, 7, 681–699 (1964)], antiserum (256 times the PCA titer) of rat against egg albumin was prepared and diluted four times with physiological saline. Male SD rats (5 weeks old) were used as the test animals in groups, each containing 4 animals. The rats were sensitized by intradermal injection of 0.05 ml of the diluted antiserum solution in the dorsal position. 48 hours after this injection, a suspension of the test compound in an aqueous 0.5% w/v tragacanth solution was orally administered to the rats, fasted for one day, and 60 minutes later they were injected in the caudal vein with 5 ml/kg body weight of physiological saline containing 0.4% w/v egg albumin and 1.0% w/v Evans Blue. 30 minutes after this last injection, the rat were sacrificed with carbon dioxide and the Evans Blue exuded in the dorsal intradermal portion was determined according to Harada's method (Harada et al., J. Pharm. Pharmac., 23, 218–219 (1971)].

The results achieved from the test groups which were treated with a test compound were evaluated to determine the inhibitory rate by comparison with the average amount of exuded dye in a control group, which was not given the test compound.

The inhibitory rate was calculated by the following equation.

Inhibitory rate (%)=(1−B/A)×100

A: amount of exuded dye in the control group
B: amount of exuded dye in the test group.
The results are shown in Table 3.

TABLE 3

| Compound of Example | Salt | Dose (p.o., mg/kg) | Inhibitory rate (%) |
|---|---|---|---|
| 1 | Oxalate | 3.2 | 52 |
| 12 | Fumarate | 12.5 | 62 |
|  |  | 3.2 | 46 |
| 22 | Oxalate | 3.2 | 51 |
| 25 | Oxalate | 3.2 | 63 |
|  |  | 0.8 | 43 |
| 26 | Oxalate | 3.2 | 61 |
|  |  | 0.8 | 49 |
| 27 | Oxalate | 3.2 | 71 |
|  |  | 0.8 | 41 |
| 34 | Oxalate | 3.2 | 76 |

TABLE 3-continued

| Compound of Example | Salt | Dose (p.o., mg/kg) | Inhibitory rate (%) |
|---|---|---|---|
| | | 0.8 | 60 |
| Prior art Compound A | | 12.5 | 48 |

Prior art compound A: Maleate of ethyl 2-[1-(2-diphenylmethoxyethyl)-4-piperidyl]acetate

TEST EXAMPLE 2

Effect on Antigen-induced Bronchoconstriction in Sensitized Guinea Pigs

The test animals used were male guinea pigs of the Hartley strain (weighing about 400 to 500 g). These animals were sensitized according to Morris' method [H. R. Morris; Br. J. Pharmac., 67, 179–184 (1979)]. The guinea pigs were subcutaneously and intraperitoneally injected twice, each time with 25 mg of egg albumin (grade 5, Sigma) at weekly intervals. 7 days after the second of these weekly injections, the animals were fasted for one day and then exposed to an aerosol of egg albumin (10 mg/ml). All of the animals so exposed responded with convulsions, indicating respiratory distress due to airway constriction, within 6 minutes.

60 minutes before the egg albumin challenge, one of the test compounds shown in the following Table 4 was administered orally to each of the animals. The compound was regarded as effective if the animal did not respond with convulsions during the 6 minutes inhalation. The results are shown in Table 4.

TABLE 4

| Compound of Example | Salt | Dose (p.o., mg/kg) | Effective rate (%) |
|---|---|---|---|
| 26 | Oxalate | 0.1 | 60 |
| 34 | | 0.4 | 80 |
| | | 0.1 | 60 |

We claim:
1. A compound of formula (I):

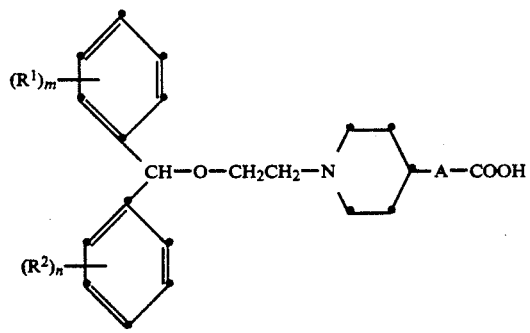

(I)

in which:
each of the groups or atoms represented by $R^1$ and $R^2$ is independently selected from the group consisting of alkyl groups having from 1 to 4 carbon atoms, alkoxy groups having from 1 to 4 carbon atoms and halogen atoms;

A represents a straight or branched chain aliphatic hydrocarbon group having from 2 to 8 carbon atoms whose chain contains at least 2 carbon atoms in a linear chain between the piperidine group and —COOH, said group being saturated or including at least one double or triple carbon-carbon bond; and m and n are independently 0, 1, 2 or 3;
and pharmaceutically acceptable salts and esters thereof.

2. The compound of claim 1, wherein A represents a vinylene group or a straight or branched chain aliphatic hydrocarbon group having from 3 to 7 carbon atoms and whose chain contains at least 2 carbon atoms in a linear chain between the piperidine group and —COOH, said group being saturated or including at least one double or triple carbon-carbon bond.

3. The compound of claim 1, wherein m and n are independently 0 or 1.

4. The compound of claim 1, wherein said ester has the formula (Ia):

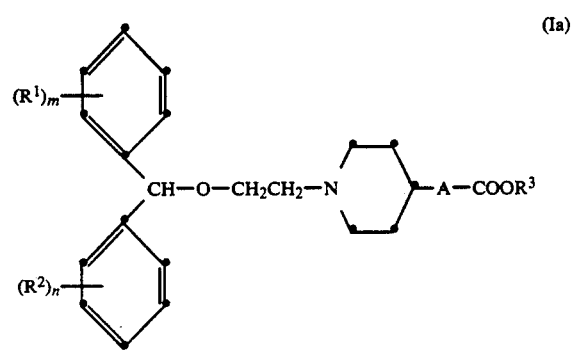

(Ia)

in which: $R^1$, $R^2$, m, n and A are as defined in claim 1 and $R^3$ represents: a $C_1$-$C_{20}$ alkyl group; a $C_3$-$C_7$ cycloalkyl group; an aralkyl group in which the aromatic group is $C_{6-14}$, which may be substituted or unsubstituted, and, if substituted, has at least one substituent selected from the group consisting of alkyl groups having from 1 to 6 carbon atoms, alkoxy groups having from 1 to 6 carbon atoms, trifluoromethyl groups, nitro groups and halogen atoms; an alkenyl group having from 2 to 6 carbon atoms; an aryl group having from 6 to 10 carbon atoms, which is unsubstituted or substituted with at least one $C_1$-$C_4$ alkyl or $C_1$-$C_4$ alkoxy group or halogen atom; a phenacyl group, which is unsubstituted or has at least one substituent selected from the group consisting of alkyl groups having from 1 to 6 carbon atoms, alkoxy groups having from 1 to 6 carbon atoms, trifluoromethyl groups, nitro groups and halogen atoms; a cyclic or acyclic terpenyl group; a terpenylcarbonyloxyalkyl or terpenyloxycarbonyloxyalkyl group; an alkoxymethyl group, in which the alkoxy part is $C_1$-$C_6$ and may itself be substituted by a single unsubstituted alkoxy group; an alkoxycarbonylmethyl group in which the alkoxy part has from 1 to 6 carbon atoms; an aliphatic acyloxymethyl group; a higher aliphatic acyloxyalkyl group in which the acyl group is a $C_2$-$C_6$ alkanoyl group, and the alkyl part is $C_2$-$C_6$; an alkoxycarbonyloxyalkyl group, in which the alkoxy part is $C_1$-$C_{10}$, and the alkyl part is $C_1$-$C_6$; a (5-alkyl- or 5-phenyl-2-oxo-1,3-dioxolen-4-yl)alkyl group in which the alkyl group is $C_1$-$C_6$; or a phthalidyl, indanyl or 2-oxo-4,5,6,7-tetrahydro-1,3-benzodioxolen-4-yl group.

5. The compound of claim 1, which has the formula (I'):

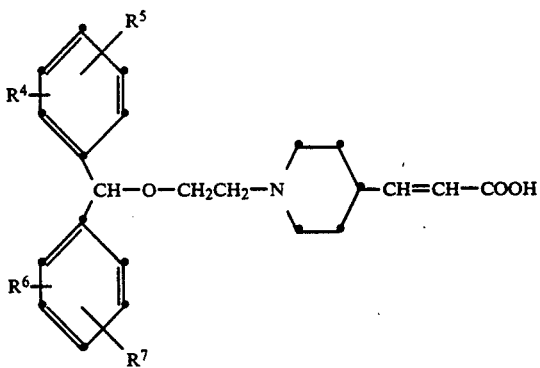

(I′)

in which $R^4$, $R^5$, $R^6$ and $R^7$ are the same or different and each represents a hydrogen atom, an alkyl group having from 1 to 4 carbon atoms, an alkoxy group having from 1 to 4 carbon atoms or a halogen atom;
and pharmaceutically acceptable salts and esters thereof.

6. The compound of claim 1, which has the formula (I″)

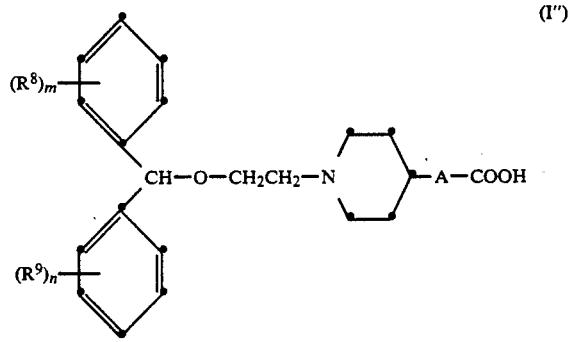

(I″)

in which: A, m and n are as defined in claim 1, except that A is not a vinylene group; and $R^8$ and $R^9$ are the same or different and each represents an alkyl group having from 1 to 4 carbon atoms, an alkoxy group having from 1 to 4 carbon atoms or a halogen atom;
and pharmaceutically acceptable salts and esters thereof.

7. The compound of claim 6, wherein A represents a straight or branched chain aliphatic hydrocarbon group having from 3 to 7 carbon atoms and whose chain contains at least 2 carbon atoms in a linear chain between the piperidine group and —COOH, said group being saturated or including at least one double or triple carbon-carbon bond.

8. The compound of claim 6, wherein m and n are independently 0 or 1.

9. The compound of claim 1, wherein $R^1$ and $R^2$ are the same or different and each represents a halogen atom.

10. The compound of claim 9, wherein $R^1$ and $R^2$ each represents a fluorine atom.

11. The compound of claim 5, wherein $R^1$ and $R^2$ are the same or different and each represents a halogen atom.

12. The compound of claim 11, wherein $R^1$ and $R^2$ each represents a fluorine atom.

13. The compound of claim 6, wherein $R^1$ and $R^2$ are the same or different and each represents a halogen atom.

14. The compound of claim 13, wherein $R^1$ and $R^2$ each represents a fluorine atom.

15. The compound of claim 1, wherein A represents an alkylene group having from 2 to 7 carbon atoms or an alkenylene group having 2 or 3 carbon atoms.

16. The compound of claim 6, wherein A represents an alkylene group having from 2 to 7 carbon atoms or an alkenylene group having 3 carbon atoms.

17. The compound of claim 1, wherein said ester is an alkyl ester having from 1 to 4 carbon atoms in the alkyl moiety or an ester which can easily be hydrolised in vivo.

18. The compound of claim 5, wherein said ester is an alkyl ester having from 1 to 4 carbon atoms in the alkyl moiety or an ester which can easily be hydrolised in vivo.

19. The compound of claim 6, wherein said ester is an alkyl ester having from 1 to 4 carbon atoms in the alkyl moiety or an ester which can easily be hydrolised in vivo.

20. The compound of claim 1, wherein:
$R^1$ and $R^2$ are the same or different and each represents a halogen atom;
A represents an alkylene group having from 2 to 7 carbon atoms or an alkenylene group having 2 or 3 carbon atoms; and
m and n are independently 0 or 1;
and $C_1$-$C_4$ alkyl esters and in vivo hydrolisable esters thereof.

21. The compound of claim 20, wherein $R^1$ and $R^2$ each represent fluorine atoms.

22. The compound of claim 6, wherein:
$R^1$ and $R^2$ are the same or different and each represents a halogen atom;
A represents an alkylene group having from 2 to 7 carbon atoms or an alkenylene group having 2 or 3 carbon atoms; and
m and n are independently 0 or 1;
and $C_1$-$C_4$ alkyl esters and in vivo hydrolisable esters thereof.

23. The compound of claim 22, wherein $R^1$ and $R^2$ each represent fluorine atoms.

24. The compound of claim 1, wherein $R^1$ and $R^2$ the same or different and each represents a fluorine or chlorine atom.

25. The compound of claim 5, wherein one of $R^4$ and $R^5$ and one of $R^6$ and $R^7$ are the same or different and each represents a fluorine or chlorine atom.

26. The compound of claim 6, wherein $R^1$ and $R^2$ are the same or different and each represents a fluorine or chlorine atom.

27. The compound of claim 1, wherein A represents an alkylene group having 3 or 5 carbon atoms.

28. The compound of claim 1, wherein said ester is an alkyl ester having from 1 to 4 carbon atoms in the alkyl moiety.

29. The compound of claim 5, wherein said ester is an alkyl ester having from 1 to 4 carbon atoms in the alkyl moiety.

30. The compound of claim 6, wherein said ester is an alkyl ester having from 1 to 4 carbon atoms in the alkyl moiety.

31. The compound of claim 1, wherein:
$R^1$ and $R^2$ are the same or different and each represents a fluorine or chlorine atom;

A represents an alkylene group having 3 or 5 carbon atoms;
m and n are independently 0 or 1;
and C$_1$–C$_4$ alkyl esters thereof.

32. The compound of claim 6, wherein:
R$^1$ and R$^2$ are the same or different and each represents a fluorine or chlorine atom;
A represents an alkylene group having 3 or 5 carbon atoms;
m and n are independently 0 or 1;
and C$_1$–C$_4$ alkyl esters thereof.

33. The compound of claim 1, selected from the group consisting of methyl 3-{1-[2-bis(4-fluorophenyl)-methoxyethyl]-4-piperidyl}acrylate and pharmaceutically acceptable salts thereof.

34. The compound of claim 1, selected from the group consisting of ethyl 3-{1-[2-bis(4-fluorophenyl)-methoxyethyl]-4-piperidyl}acrylate and pharmaceutically acceptable salts thereof.

35. The compound of claim 1, selected from the group consisting of methyl 4-{1-[2-bis(4-fluorophenyl)-methoxyethyl]-4-piperidyl}butyrate and pharmaceutically acceptable salts thereof.

36. The compound of claim 1, selected from the group consisting of ethyl 4-{1-[2-bis(4-fluorophenyl)-methoxyethyl]-4-piperidyl}butyrate and pharmaceutically acceptable salts thereof.

37. The compound of claim 1, selected from the group consisting of methyl 6-{1-[2-bis(4-fluorophenyl)-methoxyethyl]-4-piperidyl}hexanoate and pharmaceutically acceptable salts thereof.

38. The compound of claim 1, selected from the group consisting of ethyl 6-{1-[2-bis(4-fluorophenyl)-methoxyethyl]-4-piperidyl}hexanoate and pharmaceutically acceptable salts thereof.

39. The compound of claim 1, selected from the group consisting of ethyl 8-{1-[2-bis(4-fluorophenyl)-methoxyethyl]-4-piperidyl}octanoate and pharmaceutically acceptable salts thereof.

40. The compound of claim 1, selected from the group consisting of methyl 3-{1-[2-bis(4-fluorophenyl)-methoxyethyl]-4-piperidyl}-2-methylpropionate and pharmaceutically acceptable salts thereof.

41. The compound of claim 1, selected from the group consisting of ethyl 3-{1-[2-bis(4-fluorophenyl)-methoxyethyl]-4-piperidyl}-2-methylpropionate and pharmaceutically acceptable salts thereof.

42. The compound of claim 1, selected from the group consisting of ethyl 6-{1-[2-bis(4-fluorophenyl)-methoxyethyl]-4-piperidyl}-2-methylhexanoate and pharmaceutically acceptable salts thereof.

43. The compound of claim 1, selected from the group consisting of ethyl 6-{1-[2-bis(4-fluorophenyl)-methoxyethyl]-4-piperidyl}-2-hexanoate and pharmaceutically acceptable salts thereof.

44. The compound of claim 1, selected from the group consisting of ethyl 4-{1-[2-(2,4'-difluorobenzhydryloxy)ethyl]-4-piperidyl}butyrate and pharmaceutically acceptable salts thereof.

45. The compound of claim 1, selected from the group consisting of ethyl 6-{1-[2-(2,4'-difluorobenzhydryloxy)ethyl]-4-piperidyl]hexanoate and pharmaceutically acceptable salts thereof.

46. The compound of claim 1, selected from the group consisting of propyl 4-{1-[2-bis(4-fluorophenyl)-methoxyethyl]-4-piperidyl]butyrate and pharmaceutically acceptable salts thereof.

47. The compound of claim 1, selected from the group consisting of butyl 4-{1-[2-bis(4-fluorophenyl)-methoxyethyl]-4-piperidyl}butyrate and pharmaceutically acceptable salts thereof.

48. A composition for the treatment or prophylaxis of histamine-related disorders in a mammal which comprises an effective amount of an anti-histamine in admixture with a pharmaceutically acceptable carrier or diluent, wherein the anti-histamine is at least one compound selected from the group consisting of compounds of formula (I) and pharmaceutically acceptable salts and esters thereof as claimed in claim 1.

49. The composition of claim 48, wherein said anti-histamine is selected from the group consisting of compounds of formula (I) in which:
R$^1$ and R$^2$ are the same or different and each represents a fluorine or chlorine atom;
m and n are independently 0 or 1;
A represents an alkylene group having 3 or 5 carbon atoms;
and C$_1$–C$_4$ alkyl esters thereof.

50. The composition of claim 48, wherein said anti-histamine is selected from the group consisting of:
methyl 3-{1-[2-bis(4-fluorophenyl)methoxyethyl]-4-piperidyl}acrylate;
ethyl 3-{1-[2-bis(4-fluorophenyl)methoxyethyl]-4-piperidyl}acrylate;
methyl 4-{1-[2-bis(4-fluorophenyl)methoxyethyl]-4-piperidyl}butyrate;
ethyl 4-{1-[2-bis(4-fluorophenyl)methoxyethyl]-4-piperidyl}butyrate;
methyl 6-{1-[2-bis(4-fluorophenyl)methoxyethyl]-4-piperidyl} hexanoate;
ethyl 6-{1-[2-bis(4-fluorophenyl)methoxyethyl]-4-piperidyl}hexanoate;
ethyl 8-{1-[2-bis(4-fluorophenyl)methoxyethyl]-4-piperidyl}octanoate;
methyl 3-{1-[2-bis(4-fluorophenyl)methoxyethyl]-4-piperidyl}-2-methylpropionate;
ethyl 3-{1-[2-bis(4-fluorophenyl)methoxyethyl]-4-piperidyl}-2-methylpropionate;
ethyl 6-{1-[2-bis(4-fluorophenyl)methoxyethyl]-4-piperidyl}-2-methylhexanoate;
ethyl 6-{1-[2-bis(4-fluorophenyl)methoxyethyl]-4-piperidyl}-2-hexenoate;
ethyl 4-{1-[2-(2,4'-difluorobenzhydryloxy)ethyl]-4-piperidyl}butyrate;
ethyl 6-{1-[2-(2,4'-difluorobenzhydryloxy)ethyl]-4-piperidyl}hexanoate;
propyl 4-{1-[2-bis(4-fluorophenyl)methoxyethyl]-4-piperidyl}butyrate;
butyl 4-{1-[2-bis(4-fluorophenyl)methoxyethyl]-4-piperidyl}butyrate;
and salts thereof.

51. A method for the treatment or prophylaxis of histamine-related disorders in a mammal, which comprises administering to said mammal an effective amount of an anti-histamine, wherein the anti-histamine is at least one compound selected from the group consisting of compounds of formula (I) and pharmaceutically acceptable salts and esters thereof as claimed in claim 1.

52. The method of claim 51, wherein said anti-histamine is selected from the group consisting of compounds of formula (1) in which:
R$^1$ and R$^2$ are the same or different and each represents a fluorine or chlorine atom;
m and n are independently 0 or 1;

A represents an alkylene group having 3 or 5 carbon atoms;

and C$_1$-C$_4$ alkyl esters thereof.

53. The method of claim 51, wherein said anti-histamine is selected from the group consisting of:

methyl 3-{1-[2-bis(4-fluorophenyl)methoxyethyl]-4-piperidyl}acrylate;
ethyl 3-{1-[2-bis(4-fluorophenyl)methoxyethyl]-4-piperidyl}acrylate;
methyl 4-{1-[2-bis(4-fluorophenyl)methoxyethyl]-4-piperidyl}butyrate;
ethyl 4-{1-[2-bis(4-fluorophenyl)methoxyethyl]-4-piperidyl}butyrate;
methyl 6-{1-[2-bis(4-fluorophenyl)methoxyethyl]-4-piperidyl}hexanoate;
ethyl 6-{1-[2-bis(4-fluorophenyl)methoxyethyl]-4-piperidyl}hexanoate;
ethyl 8-{1-[2-bis(4-fluorophenyl)methoxyethyl]-4-piperidyl}octanoate;
methyl 3-{1-[2-bis(4-fluorophenyl)methoxyethyl]-4-piperidyl}-2-methylpropionate;
ethyl 3-{1-[2-bis(4-fluorophenyl)methoxyethyl]-4-piperidyl}-2-methylpropionate;
ethyl 6-{1-[2-bis(4-fluorophenyl)methoxyethyl]-4-piperidyl}-2-methylhexanoate;
ethyl 6-[1-[2-bis(4-fluorophenyl)methoxyethyl]-4-piperidyl}-2-hexenoate;
ethyl 4-{1-[2-(2,4'-difluorobenzhydryloxy)ethyl]-4-piperidyl}butyrate:
ethyl 6-{1-[2-(2,4'-difluorobenzhydryloxy)ethyl]-4-piperidyl}hexanoate;
propyl 4-{1-[2-bis(4-fluorophenyl)methoxyethyl]-4-piperidyl}butyrate;
butyl 4-[1-[2-bis(4-fluorophenyl)methoxyethyl]-4-piperidyl}butyrate;
and salts thereof.

54. The compound of claim 1, wherein A is selected from the group consisting of vinylene, trimethylene, 1-methyltrimethylene, 1-methyltetramethylene and 1-propylene.

55. The compound of claim 54, wherein R$^1$ and R$^2$ are each independently selected from the group consisting of methyl, ethyl, propyl, isopropyl, butyl, isobutyl, methoxy, ethoxy, propoxy, isopropoxy, butoxy, isobutoxy, fluorine, and chlorine; m is 1 and n is 1.

* * * * *